US012663428B2

(12) United States Patent
Kawabe

(10) Patent No.: US 12,663,428 B2
(45) Date of Patent: Jun. 23, 2026

(54) BLOOD COAGULATION TIME MEASUREMENT METHOD

(71) Applicant: SEKISUI MEDICAL CO., LTD., Chuo-ku (JP)

(72) Inventor: Toshiki Kawabe, Chuo-ku (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 915 days.

(21) Appl. No.: 17/788,869

(22) PCT Filed: Dec. 25, 2020

(86) PCT No.: PCT/JP2020/048676
§ 371 (c)(1),
(2) Date: Jun. 24, 2022

(87) PCT Pub. No.: WO2021/132552
PCT Pub. Date: Jul. 1, 2021

(65) Prior Publication Data
US 2023/0341423 A1      Oct. 26, 2023

(30) Foreign Application Priority Data
Dec. 26, 2019    (JP) ................................. 2019-237427

(51) Int. Cl.
*G01N 33/86*      (2006.01)
*G01N 21/77*      (2006.01)
(52) U.S. Cl.
CPC ............. *G01N 33/86* (2013.01); *G01N 21/77* (2013.01)
(58) Field of Classification Search
CPC . G01N 33/86; G01N 33/4905; C12N 15/8234
See application file for complete search history.

(56) References Cited

U.S. PATENT DOCUMENTS

| | | | |
|---|---|---|---|
| 6,342,657 B1 * | 1/2002 | Thomas ............. | C12N 15/8234 435/320.1 |
| 2014/0255254 A1 * | 9/2014 | Yamaguchi ........ | G01N 33/4905 422/73 |
| 2015/0104351 A1 | 4/2015 | Makino et al. | |
| 2018/0045709 A1 | 2/2018 | Shima et al. | |

FOREIGN PATENT DOCUMENTS

| | | | | |
|---|---|---|---|---|
| JP | 6-249855 A | 9/1994 | | |
| JP | 2019-86517 A | 6/2019 | | |
| WO | WO-2007086069 A1 * | 8/2007 | ............. | G01N 33/86 |
| WO | WO 2013/187210 A1 | 12/2013 | | |
| WO | WO-2015159516 A1 * | 10/2015 | ......... | G01N 33/4905 |
| WO | WO 2016/170944 A1 | 10/2016 | | |

OTHER PUBLICATIONS

International Search Report issued Mar. 23, 2021 in PCT/JP2020/048676, filed on Dec. 25, 2020, 2 pages.

* cited by examiner

*Primary Examiner* — Lam S Nguyen
(74) *Attorney, Agent, or Firm* — Oblon, McClelland, Maier & Neustadt, L.L.P.

(57) ABSTRACT

Provided is a blood coagulation time measurement method. In the method, reaction X(i) is acquired through smoothing and zero-point adjustment of a measured value P(i) for coagulation reaction of a blood specimen, and then an integration ratio Z(i) of the reaction X(i) is acquired. These values are used to calculate an index for coagulation time Tc calculation, and it is determined whether or not the index satisfies the criteria. The procedure is sequentially repeated until an index that satisfies the criteria is obtained.

11 Claims, 12 Drawing Sheets

A

B

C

D

Sample 11

| k | 1 | 2 | 3 | 4 | 5 | 6 | 7 | 8 |
|---|---|---|---|---|---|---|---|---|
| Zs[k] | 1.036 | 1.031 | 1.026 | 1.021 | 1.016 | 1.011 | 1.006 | 1.001 |
| te[k] | 252.4 | 262.2 | 275.8 | 292.5 | 315.2 | 341.4 | | |
| tc[k] | 219.3 | 225.3 | 233.3 | 242.3 | 253.4 | 264.3 | | |
| X(te[k]) | 2217 | 2583 | 3096 | 3711 | 4514 | 5329 | | |
| R[k] | — | 116.5 | 119.9 | 119.9 | 121.6 | 118.1 | | |
| te[k]-te[k-1] | — | 9.8 | 13.6 | 16.7 | 22.7 | 26.2 | | |
| tc[k]-tc[k-1] | — | 6 | 8 | 9 | 11.1 | 10.9 | | |
| TR[k] | — | 61.2 | 58.8 | 53.9 | 48.9 | 41.6 | | |

Sample 12

| k | 1 | 2 | 3 | 4 | 5 | 6 | 7 | 8 |
|---|---|---|---|---|---|---|---|---|
| Zs[k] | 1.036 | 1.031 | 1.026 | 1.021 | 1.016 | 1.011 | 1.006 | 1.001 |
| te[k] | 39.3 | 39.8 | | | | | | |
| tc[k] | 30.9 | 30.9 | | | | | | |
| X(te[k]) | 640 | 645 | | | | | | |
| R[k] | — | 100.8 | | | | | | |
| te[k]-te[k-1] | — | 0.5 | | | | | | |
| tc[k]-tc[k-1] | — | 0 | | | | | | |
| TR[k] | — | 0.0 | | | | | | |

BLOOD COAGULATION TIME MEASUREMENT METHOD

TECHNICAL FIELD

The present invention relates to a blood coagulation time measurement method.

BACKGROUND ART

The blood coagulation test is a test for diagnosing a blood coagulation ability of a patient by adding a predetermined reagent to a blood specimen of the patient and measuring, for example, the blood coagulation time. Typical examples of the blood coagulation time include a prothrombin time (PT), an activated partial thromboplastin time (APTT), and a thrombin time. By the blood coagulation test, the hemostatic ability or fibrinolytic capacity of a patient can be investigated. The abnormality of the blood coagulation ability mainly causes a prolonged coagulation time. Examples of the cause of a prolonged coagulation time include influence of a coagulation inhibitor, reduction of components involved in coagulation, congenital deficiency of blood coagulation factors, and acquired autoantibodies that inhibit coagulation reaction.

In recent years, an automatic analyzer that performs automatic measurement of a blood coagulation test has been widely used, and the blood coagulation test can be easily performed. For example, with a certain type of automatic analyzer, a mixture obtained by adding a reagent to a blood specimen is exposed to light, and the coagulation reaction of the blood specimen is measured on the basis of the change in the obtained amount of scattered light. In a normal blood coagulation reaction, at the time point when a certain period of time has elapsed from addition of a reagent, the amount of scattered light drastically increases due to the progress of coagulation, and after that, as the coagulation reaction comes closer to the termination, the amount of scattered light is saturated and reaches the plateau. The blood coagulation time can be measured on the basis of such a time change in the amount of scattered light. As the method for calculating the coagulation time by an automatic analyzer, several techniques such as the percent detection method, and the differential method have been used. Among them, in the percent detection method, the change in the amount of scattered light per unit time is large, and by detecting, for example, the point when the amount of scattered light reaches 50% of the maximum amount, the coagulation time can be considerably accurately measured even in an abnormal specimen such as a low fibrinogen specimen, a chylous specimen, or a hemolytic specimen.

In addition, the photometric data by an analyzer includes various noises due to, for example, the analyzer, the reagent, and the conditions of the specimen, and such noises may lead to false detection of a coagulation time. In the automatic analysis of a blood specimen, it is required to eliminate the adverse effects of noises and to calculate a reliable coagulation time. A method for avoiding the false detection of a coagulation time due to the noises of photometric data has been devised. Patent Literature 1 discloses a blood coagulation time measurement method, in which scattered light amount data obtained in real time from an analyzer is smoothed and origin adjusted to be taken as the reference data X, from the reference data, reference integral data Y that is obtained by the further integration and reference ratio data Z that is a ratio of integrated values in adjacent minute times of the reference data are calculated, among the time points when the reference ratio data Z becomes a predetermined constant reference ratio data value Zs, a reference data value Xd is selected at the time point after the peak of the reference ratio data Z and at the time point when the reference integral data Y becomes a predetermined threshold Ys or more, and a time from the mixing time point to the time point to which the value of 1/N (N is a constant integer of 1 or more) of the Xd corresponds is taken as the coagulation time.

CITATION LIST

Patent Literature

Patent Literature 1: JP H06-249855 A

SUMMARY OF INVENTION

Technical Problem

The present invention relates to a blood coagulation time measurement method, by which a coagulation time of blood specimens showing various blood coagulation reaction curves can be accurately measured.

Solution to Problem

Accordingly, the present invention provides the following:

<1> A blood coagulation time measurement method, including the steps of:

[1] acquiring reaction X(i) through smoothing and zero-point adjustment of a measured value P(i) for coagulation reaction of a blood specimen;

[2] acquiring an integration ratio Z(i) of the reaction X(i), wherein the Z(i) is a ratio of an integrated value of X in a first measurement section to an integrated value of X in a second measurement section adjacent to the first measurement section;

[3] calculating parameters te[k], X(te[k]), tc[k], te[k−1], X(te[k−1]), and tc[k−1], wherein k is an integer of 2 or more, te[k] and te[k−1] are a measurement time at i satisfying Z(i)<Zs[k] and a measurement time at i satisfying Z(i)<Zs[k−1], respectively, X(te[k]) and X(te[k−1]) are reactions X at te[k] and te[k−1], respectively, tc[k] and tc[k−1] are a measurement time at i satisfying X(i)={X(te[k])×Q %} and a measurement time at i satisfying {X(te[k−1])×Q %}, respectively, and $$1 < Q < 100;$$

[4] calculating an index R[k] and/or an index TR[k], wherein $$R[k] = X(te[k]) / X(te[k-1]) \qquad (2)$$

$$TR[k] = \Delta tc[k] / \Delta te[k] \qquad (5)$$

$$\Delta tc[k] = tc[k] - tc[k-1] \qquad (3)$$

$$\Delta te[k] = \Delta te[k] - te[k-1]; \qquad (4)$$

[5] determining the tc[k] or the tc[k−1] as a coagulation time Tc in a case where the R[k] and/or TR[k] satisfy a predetermined condition.

<2> The method as described in <1>, in which the steps [3] to [5] are repeated with k=k+1 in a case where the R[k] or TR[k] does not satisfy the predetermined condition in the step [5].

<3> The method as described in <1> or <2>, in which Zs[k]<Zs[k−1], Zs[k] is greater than 1, and Zs[1] is 1.100 or less.

<4> The method as described in any one of <1> to <3>, in which k is 10 or less.

<5> The method as described in any one of <1> to <4>, in which a difference between Zs[k−1] and Zs[k] is from 0.050 to 0.001.

<6> The method as described in any one of <1> to <5>, in which Z(i) is represented by the following equation:

$$Z(i) = \{X(i+1) + X(i+2) + ... + X(i+m)\}/ \qquad (1)$$

$$\{X(i-m) + X(i-m+1) + ... + X(i-1)\}(m = 10 \text{ to } 30).$$

<7> The method as described in any one of <1> to <6>, in which the step [3] is performed after i reaches a predetermined calculation start point s.

<8> The method as described in <7>, in which the calculation start point s is a measurement point after a time when a rate of coagulation reaction becomes a maximum.

<9> The method as described in <7> or <8>, further including detecting, as the calculation start point s, a later one of measurement points that satisfy V(i)=Vs when the number of measurement points between two points when V(i)=Vs is satisfied (V(i) is a differential value of the reaction X(i)) exceeds a predetermined value.

<10> The method as described in <7>, in which the calculation start point s is a measurement point after Z(i) acquired in the step [2] has reached its peak.

<11> The method as described in any one of <1> to <10>, in which the steps [1] and [2] and the steps [3] to [5] are performed in parallel.

<12> The method as described in any one of <2> to <11>, further including acquiring a result that Tc is not normally determined when Tc is not determined through the repetition of the steps [3] to [5].

Advantageous Effects of Invention

According to the method of the present invention, a coagulation time of a blood specimen showing various blood coagulation reaction curves, including a normal specimen and an abnormal specimen can be accurately measured. Further, in a case where a large number of specimens are analyzed in real time by an automatic analyzer, the method of the present invention prevents the false detection of a coagulation time, optimizes the analysis time per specimen, and improves the analysis efficiency.

DESCRIPTION OF EMBODIMENTS

1. Blood Coagulation Reaction Measurement

Figure 1:
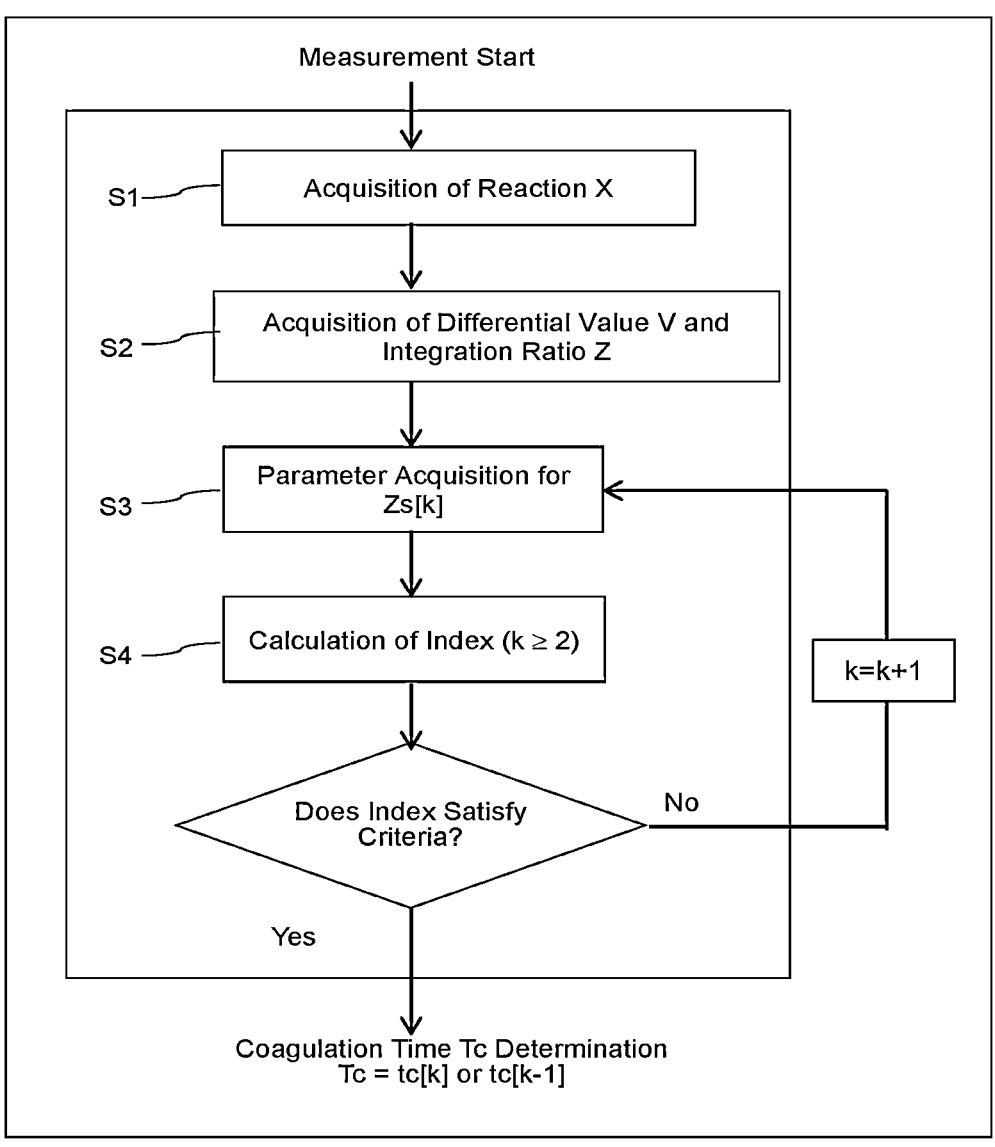
FIG. 1 shows a basic flow of one embodiment of the blood coagulation time measurement method according to the present invention.

In the blood coagulation test, a predetermined reagent is added to a blood specimen, blood coagulation reaction after the addition is measured, and a blood coagulation time is measured from the coagulation reaction. In the measurement of the coagulation reaction, a common means, for example, an optical means for measuring, for example, an amount of scattered light, transmittance, or absorbance, or a mechanical means for measuring a viscosity of blood plasma may be used. The coagulation reaction curve of a normal blood specimen basically shows a sigmoid shape although depending on the measuring means. For example, in general, the coagulation reaction curve based on the amount of scattered light of a normal specimen drastically increases at the time point when a certain period of time has elapsed from addition of a reagent due to the progress of coagulation, and then reaches the plateau as the coagulation reaction comes closer to the termination. Meanwhile, the coagulation reaction curve of an abnormal specimen having abnormal coagulation shows various shapes depending on the cause of the abnormality, such as a delay in the rise time or a gradual increase of the curve. The variety of coagulation reaction curve of an abnormal specimen makes the accurate measurement of a coagulation time by an automatic analyzer difficult.

In the conventional general blood coagulation time measurement, at least the data up to the termination of coagulation reaction are acquired, and the coagulation time is calculated on the basis of the acquired data. There are, for example, a technique for determining, as the coagulation time, a time point when the coagulation reaction curve reaches the maximum rate between the time point of the addition of a reagent and the time point of the termination of coagulation reaction, after the time point when the amount of scattered light is saturated is determined as the termination of coagulation reaction (differential method);, and a technique for determining a time point when the amount of scattered light reaches 1/Q at the time point of the termination of coagulation reaction as the coagulation time (percent detection method, see Patent Literature 1). However, due to the abnormal shape and noise of the coagulation reaction curve of an abnormal specimen as described above, false detection of the termination of coagulation reaction is generated, and for example, the termination of coagulation reaction may be detected at the early time point, or the termination of coagulation reaction may not be detected. As a result of such false detection of the termination of coagulation reaction, an inaccurate coagulation time is calculated.

In an automatic analyzer, in order to efficiently analyze a large number of specimens, it is desirable to immediately finish the measurement when it is determined that the coagulation reaction of one specimen is terminated, and to start the measurement of the following specimen. However, in such a technique, there is a risk that the false detection of the termination of coagulation reaction at the early time point described above finishes the measurement even in the course of the measurement, and as a result of which the collection of necessary data is missed out. Meanwhile, if the measurement time per specimen is fixed at a sufficiently long period of time, the missed-out collection of data due to the false detection of the termination of coagulation reaction can be prevented, however, such a technique reduces the overall analysis efficiency because the measurement time is unnecessarily long for many specimens.

For example, in a case where a coagulation time of a specimen having a small change in the coagulation reaction curve, such as a factor VIII (FVIII)-deficient specimen is measured by the method disclosed in Patent Literature 1, the appropriate value of the reference ratio data value Zs is relatively small (for example, 1.01), and this means that it takes a relatively long period of time to measure the coagulation reaction in the measurement of coagulation time of the specimen. Meanwhile, the Zs suitable for a normal specimen is a larger value (around 1.05), and this means that the coagulation time can be calculated with shorter coagulation reaction measurement for a normal specimen. Accordingly, in a case where the coagulation time measurement of any specimens including normal specimens and abnormal specimens is performed in accordance with the method disclosed in Patent Literature 1 by using an automatic analyzer, the relatively long measurement time for some abnormal specimens has to be applied also to many normal specimens. This cannot be deemed to be an efficient analysis method.

The blood coagulation time measurement method according to the present invention prevents the false detection of coagulation time due to the abnormal shape of the coagulation reaction curve as described above, and enables the accurate coagulation time measurement. Further, according to the present invention, the measurement time can be optimized for various blood specimens including a normal specimen and an abnormal specimen so that the minimum coagulation reaction measurement time required for coagulation time measurement is applied to each of the blood specimens.

In the blood coagulation time measurement method according to the present invention (hereinafter, also referred to as "the method of the present invention"), the coagulation reaction of a test blood specimen mixed with a reagent is measured. The blood coagulation time is measured on the basis of the time-series data of the coagulation reaction obtained by this measurement. Examples of the blood coagulation time measured by the method of the present invention include a prothrombin time (PT), an activated partial thromboplastin time (APTT), and a coagulation time in measurement of fibrinogen concentration (Fbg).

In the method of the present invention, as the test blood specimen, blood plasma of a subject is preferably used. Hereinafter, a blood specimen may also be simply referred to as a specimen. Into the specimen, an anticoagulant agent that is usually used in a coagulation test can be added. For example, after collecting a blood sample by using a blood collection tube in which sodium citrate has been put, the collected blood sample is centrifuged to obtain blood plasma.

A reagent for measuring coagulation time is added to the test specimen to start blood coagulation reaction. The coagulation reaction of the mixture after addition of the reagent can be measured. The reagent to be used for measuring a coagulation time can be arbitrarily selected in accordance with the measurement purpose. Various kinds of reagents for measuring coagulation times are available on the market (for example, a reagent for measuring APTT, Coagpia APTT-N manufactured by Sekisui Medical Co., Ltd.) In the measurement of the coagulation reaction, a common means, for example, an optical means for measuring, for example, an amount of scattered light, transmittance, or absorbance, or a mechanical means for measuring a viscosity of blood plasma may be used. The start point of the coagulation reaction can be typically defined as the time point when a reagent is mixed with a specimen and the coagulation reaction starts, however, other timings may be defined as the start point of the reaction. The time for continuing the measurement of the coagulation reaction can be, for example, around several tens of seconds to 7 minutes from the time point of mixing the specimen with the reagent. This measurement time may be a fixed value arbitrarily determined, but may be up to the time point when the termination of the coagulation reaction of each specimen is detected. During the measurement time, the measurement (photometry when optically detected) of the progress state of coagulation reaction can be repeatedly performed at predetermined intervals. For example, the measurement may be performed at 0.1-second intervals. The mixture is measured under normal conditions, for example, at a temperature of 30° C. or more and 40° C. or less, and preferably 35° C. or more and 39° C. or less. Further, various kinds of conditions for measurement can be appropriately set depending on, for example, the test specimen, the reagent, or the measuring means.

A series of operations in the above-described coagulation reaction measurement may be performed by using an automatic analyzer. As one example of the automatic analyzer, a blood coagulation automated analyzer, CP3000 (manufactured by Sekisui Medical Co., Ltd.) can be mentioned. Alternatively, some of the operations may be performed manually. For example, a test specimen is prepared by a person, and the subsequent operations can be performed by an automatic analyzer.

1. Measurement of Blood Coagulation Time

Hereinafter, the present invention will be described with reference to a basic flow of one embodiment of the blood coagulation time measurement method according to the present invention shown in FIG. 1.

1.1 Acquisition of Reaction X, Differential Value V, and Integration Ratio Z

In the method of the present invention, measured values P(i) (for example, photometric values of an amount of scattered light) for coagulation reaction from the start point of the reaction are sequentially acquired by an analyzer. Herein, the "i" represents a measurement point number. For example, if the measurement (photometric) interval is 0.1 seconds, the P(i) represents the measured value 0.1×i seconds after the start of measurement.

Figure 2:
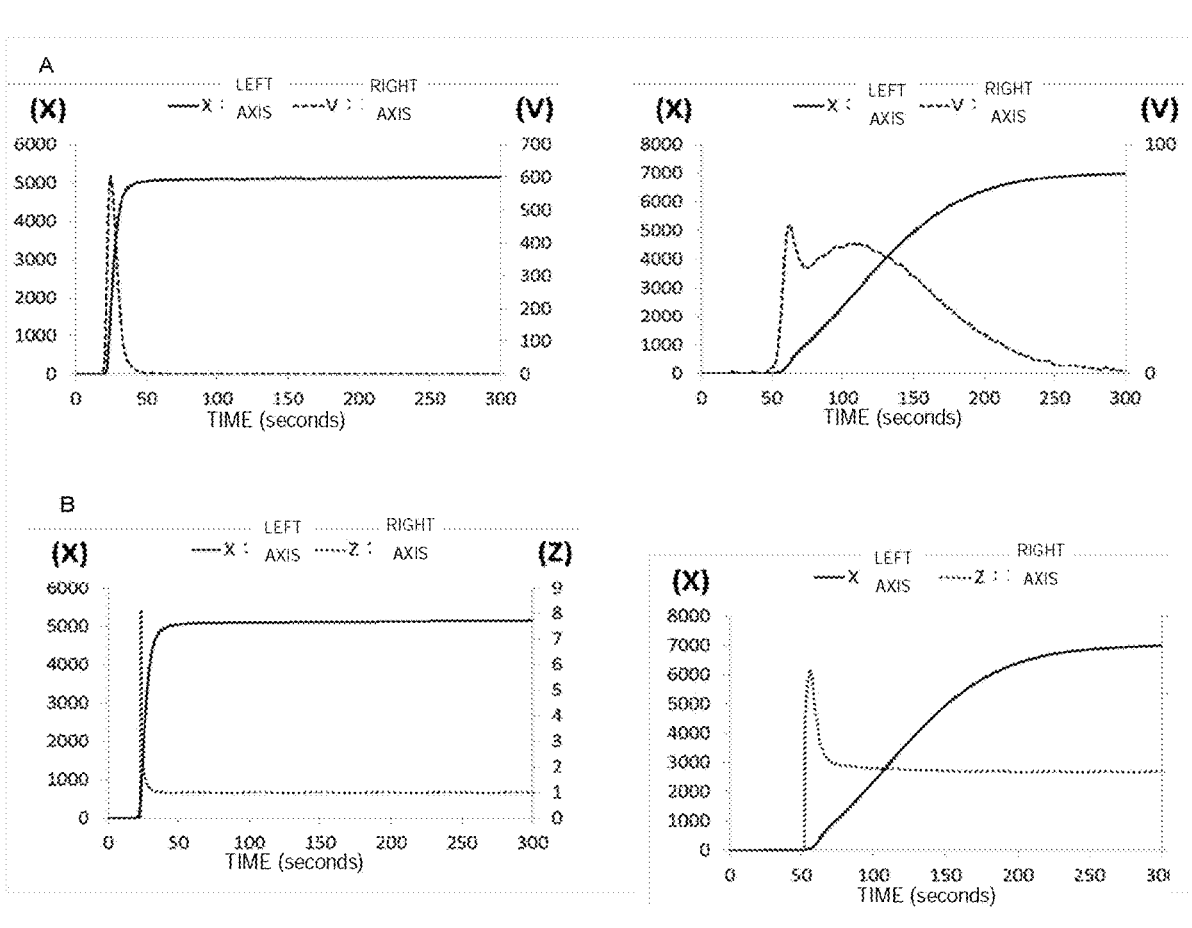
FIG. 2 shows A: reaction X and differential value V, and B: reaction X and integration ratio Z. In both A and B, the left side shows a normal specimen, and the right side shows an FVIII-deficient specimen.

Since the measured value P(i) includes the noise during the photometry and the fluctuations having no relation to reaction that appears immediately after the start of the photometry, the measured value is subjected to smoothing processing by a known method. Further, in a case where the coagulation reaction is measured by an amount of scattered light, zero-point adjustment processing that subtracts an amount of scattered light derived from a reaction mixture before the reaction is performed. Accordingly, the acquired time-series measured values P(i) are sequentially smoothed and zero-point adjusted, and reaction X(i) is acquired (step S1). Any one of various known methods for removing noise can be used for the smoothing processing of the measured value. Examples of the smoothing processing include filtering processing, and processing that determines a differential value by, for example, calculation of the difference value and the average tilt in a section to be described later, and then integrates the determined value. In the zero-point adjustment, for example, the smoothed measured value may be adjusted so that the value at the start point of the measurement becomes 0. Further, the measured value P(i) may be subjected to initial fluctuation removal processing. The initial fluctuation removal processing may be performed so that all of the values from the start point of the photometry to the predetermined initial fluctuation removal time become 0. As shown in FIG. 2, basically, the reaction X(i) makes up a smoothed and zero-point-adjusted coagulation reaction curve.

Next, an integration ratio Z(i) of the reaction X(i) is acquired from the determined reaction X(i) (step S2). Further, a differential value V(i) of the reaction X(i) may be acquired. The differential value V(i) can be used for detection of the calculation start point s to be described later.

The differential value V(i) can be obtained by primary differentiation of the reaction X(i). The differential processing can be performed by any technique, but can be performed, for example, by calculation of an average tilt value in a section. In the calculation of an average tilt value in a section, a certain number of measurement points before and after each measurement point i, for example, 2K+1 measurement points from i−K to i+K can be used. For example, five measurement points of i−2, i−1, i, i+1, and i+2 can be used. The average tilt value means a tilt value when these multiple measurement points are linearly approximated. As the calculation method of the linear approximation, a conventional method such as a method of least squares can be used. The average tilt value of these measurement points can be regarded as the primary differential value at the measurement point i.

The integration ratio Z(i) is a ratio of an integrated value of X in a first measurement section to an integrated value of reaction X in a second measurement section adjacent to the first measurement section. More specifically, Z(i) is a ratio of an integrated value of reaction X in a first measurement section before the measurement point i (for example, X(i−m)

to X(i−1) at measurement points [i−m] to [i−1]) to an integrated value of reaction X in a second measurement section after the measurement point i(for example, X(i+1) to X(i+m) at measurement points [i+1] to [i+m]). In this regard, the first measurement section and the second measurement section preferably have the same length. That is, when reaction X at a measurement point i is X(i), and m is a constant, the integration ratio Z(i) at the measurement point i is calculated by the following equation (1).

$$Z(i) = \{X(i+1) + X(i+2) + \ldots + X(i+m)\} / \qquad (1)$$
$$\{X(i-m) + X(i-m+1) + \ldots + X(i-1)\}$$

In the equation (1), m is preferably set so that the time width of the minute measurement section is from 1 second to 3 seconds. That is, if the measurement (photometry) time interval is 0.1 seconds, m is preferably from 10 to 30, and if the measurement (photometry) time interval is 0.2 seconds, m is preferably from 5 to 15. The optimum value of m may be selected so that an appropriate coagulation time can be calculated in consideration of the measurement conditions.

Accordingly, after X(i+m) is acquired at the measurement point i+m as the $(2m+1)^{th}$ data for X, the calculation of the integration ratio Z(i) can be executed. However, it is preferable that in order to avoid the influence of the fluctuation of X in an initial reaction stage, the calculation of Z(i) is started under the condition that all the values from X(i−m) to X(i−1) are the predetermined threshold Xs or more. Since the reaction curve by scattered light measurement is sigmoid, in general, once X(i) exceeds Xs, X(i)>Xs continues thereafter. In a case where X(i)≤Xs is obtained after X(i)>Xs has been obtained, the data can be considered abnormal. Xs is preferably from 10% to 50% of the maximum value of expected reaction X. For example, in a case where the maximum value of reaction X is estimated to be around 700, Xs is preferably from 70 to 350.

With the above procedure, the reaction X(i), the differential value V(i), and the integration ratio Z(i) at each measurement point i can be obtained. With reference to FIG. 2, relative difference in each shape of the reaction X, the differential value V, and the integration ratio Z between the normal specimen having a normal APTT and the FVIII-deficient specimen as an example having a prolonged APTT (hereinafter, referred to as "prolongation specimen") will be described. FIG. 2A shows the reaction X and the differential value V, and FIG. 2B shows the reaction X and the integration ratio Z. In both FIG. 2A and FIG. 2B, the left is a normal specimen, and the right is a prolongation specimen. The horizontal axis shows a time converted from the start point of the reaction.

Reaction X: As shown in FIG. 2A, X makes up a smoothed and zero-point-adjusted coagulation reaction curve. In the normal specimen (left in FIG. 2A), the rising point of X is fast and the tilt of increasing is large. However, in the prolongation specimen (right in FIG. 2A), the rising point of X is slow and the tilt of increasing is small.

Differential value V: In the normal specimen (left in FIG. 2A), the top position of the V peak is high, and the shape is almost bilaterally symmetrical. However, in the prolongation specimen (left in FIG. 2A), the top position of the V peak is low (smaller than 1/6 of the normal specimen in this example), the shape is bilaterally asymmetrical, and the peak is not one but shows a bimodal peak shape.

Integration ratio Z: In the normal specimen (left in FIG. 2B), the maximum value of Z reaches around 8 at the rise time of a reaction curve, and then the Z rapidly decreases toward 1. On the other hand, in the prolongation specimen (right in FIG. 2B), the maximum value of Z is around 2.5, and then the Z gradually decreases. In any case, the integration ratio Z comes closer to 1 as the coagulation reaction curve comes closer to the plateau (the blood coagulation reaction comes closer to the termination).

1.2 Calculation of Coagulation Time Tc 1.2.1 Determination of Calculation Start Point In the method of the present invention, the coagulation time Tc is calculated by using the above-described values of the reaction $X(i)$, the differential value $V(i)$, and the integration ratio $Z(i)$. In the method of the present invention, acquisition of X, V, and Z can be performed in parallel with the coagulation reaction measurement procedure to be described later. First, the timing of starting the calculation processing of coagulation time Tc, that is, the calculation start point s is determined on the basis of the X, V, and Z acquired so far.

In one example, any measurement point after Z reaches the peak can be taken as the calculation start point s. For example, after Z reaches the threshold, a measurement point that passes through the peak and reaches the threshold again can be taken as the calculation start point s. When taking FIG. 2B as an example, after the integration ratio Z reaches 2, the measurement point that passes through the peak and reaches 2 again can be taken as the calculation start point s.

In another example, a measurement point at which the coagulation reaction rate reaches the maximum value Vmax is determined and is taken as the calculation start point s. In the simplest case, the measurement point corresponding to the first peak top in a curve made up of $V(i)$ acquired sequentially can be taken as the calculation start point s corresponding to Vmax.

Figure 3:
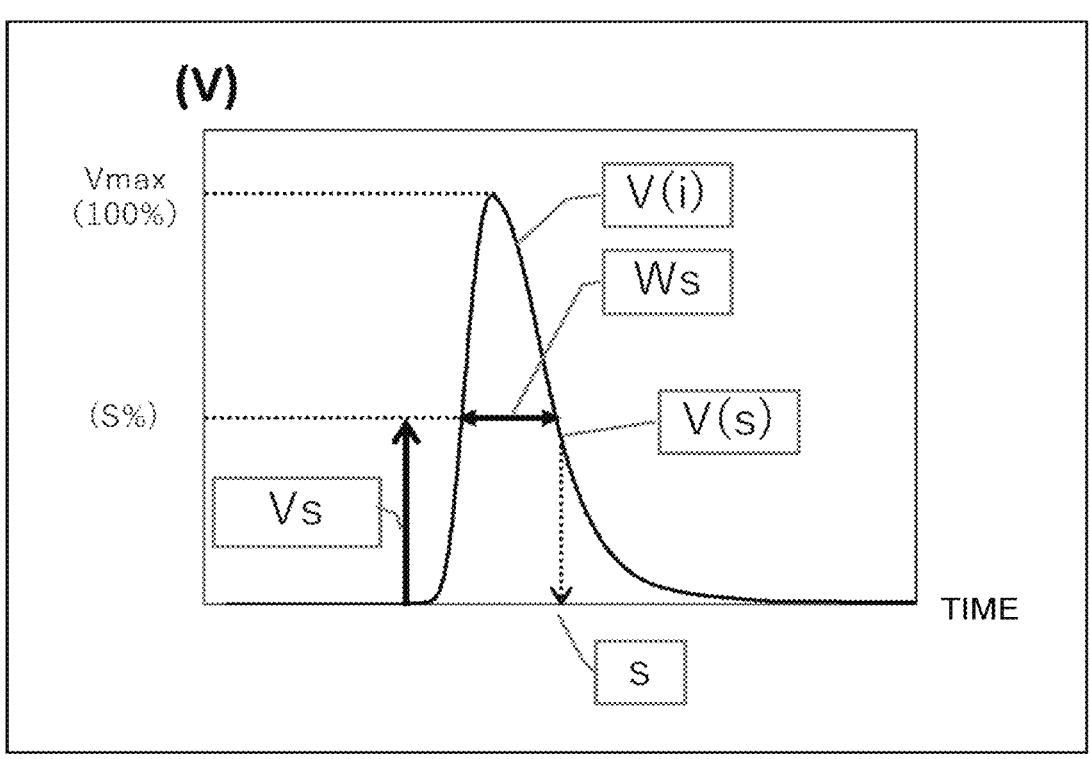
FIG. 3 is a conceptual diagram showing a technique for detecting a calculation start point s based on a peak width of V.

In addition, when the calculation start point s is determined, it is desirable to eliminate the influence of the false detection of Vmax and the fluctuation caused by noise, which can be generated in a case where the coagulation reaction rate curve is bimodal (for example, right in FIG. 2A) as often observed in a coagulation factor-deficient specimen. Accordingly, in a preferred example, the measurement point when the sequentially acquired $V(i)$ exceeds a predetermined value, then passes through the peak and reaches a predetermined condition can be taken as the calculation start point s. FIG. 3 indicates a conceptual diagram showing one example of a determination technique of the calculation start point s.

FIG. 3 shows $V(i)$ and parameters used to determine the calculation start point s. The $V(i)$ forms a curve having a peak value Vmax. Vs is a value of S % when Vmax is set to 100%. The $V(i)$ reaches Vs once, then passes through the peak and reaches Vs again at $V(s)$. At this time, when the peak width Ws, which is a width (the number of measurement points) between two points when $V(i)=Vs$, is satisfied exceeds a predetermined value, the measurement point s at the $V(s)$ is detected as the calculation start point s.

1.2.2 Parameter Acquisition

Next, parameters required for Tc calculation are acquired (step S3).

First, a measurement time (time from the start point of reaction) te[1] at a measurement point when $Z(i)$ for the first time reaches a value less than the predetermined first threshold Zs[1] ($Z(i)<Zs[1]$) after the calculation start point s is detected. If necessary, acquisition of the $Z(i)$ is continued until $Z(i)<Zs[1]$ is satisfied.

When te[1] is detected, X(te[1]), which is reaction X at te[1] is determined. Next, a measurement time tc[1] at a measurement point corresponding to X(i) having or approximating to the value of Q % of X(te[1]) is detected (where $tc[1]<te[1]$ is obtained). For example, a time tc[1] that satisfies $X(tc[1])=\{X(te[1])\times Q \%\}$ can be detected. Further, for example, a value closest to $\{X(te[1])\times Q \%\}$ can be accepted as the X(tc[1]). Furthermore, for example, when $X(tc'[1])<\{X(te[1])\times Q \%\} <X(tc''[1])$ (tc'[1] and tc''[1] are times at adjacent measurement points) is satisfied, either tc'[1] or tc''[1] can be detected as the tc[1]. In a case where the measurement (photometry) interval is sufficiently short (for example, 0.1 seconds), there is no significant difference in the final calculation value of Tc, and thus, either tc'[1] or tc''[1] may be selected. Q may be any value of $0<Q<100$, preferably from 10 to 80, and more preferably from 20 to 70 (for example, 50).

Figure 4:
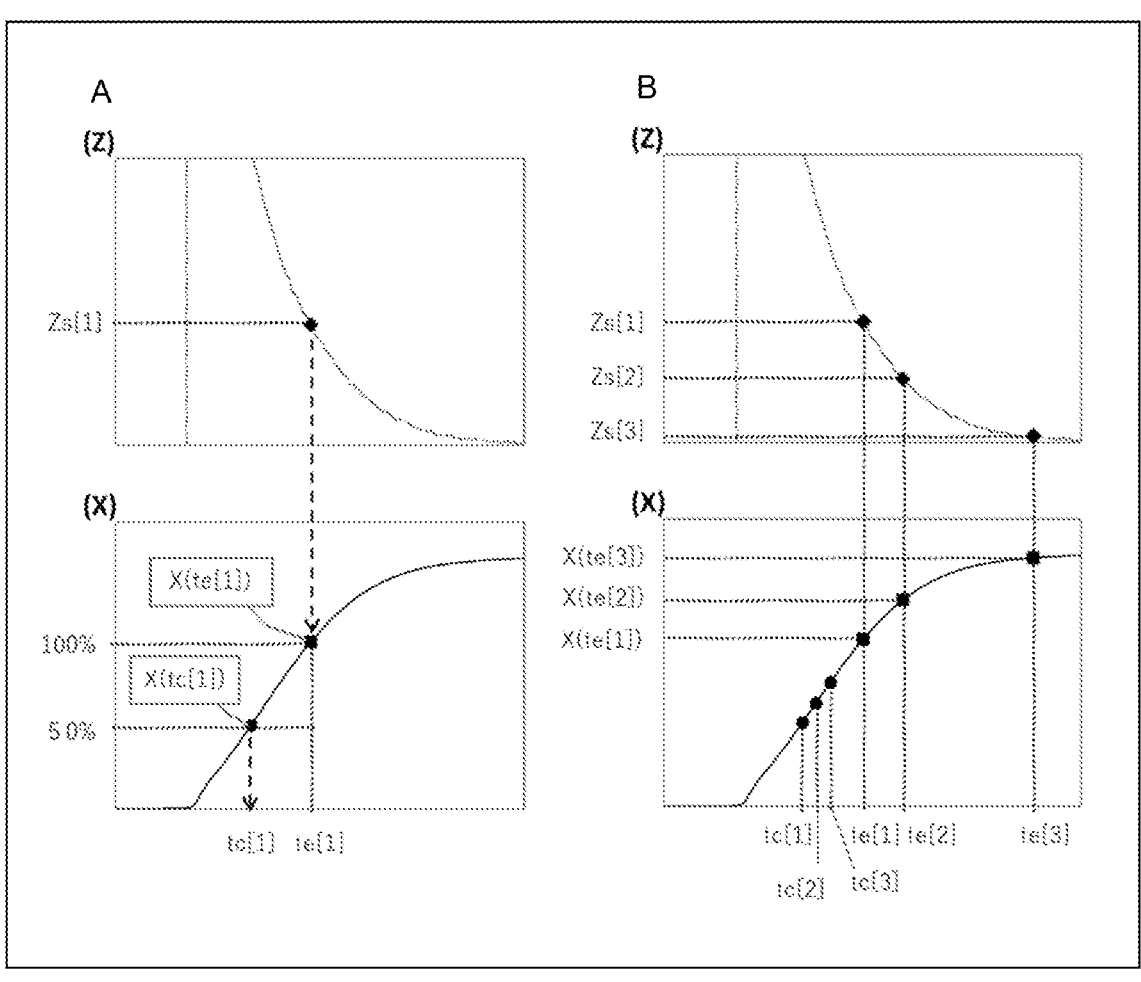
FIG. 4 shows examples of A: Zs[1], and corresponding te[1], X(te[1]), tc[1], and X(tc[1]), and B: Zs[1] to Zs[3], and corresponding te[1] to te[3], X(te[1]) to X(te[3]), and tc[1] to tc[3].

In FIG. 4A, a conceptual diagram showing the relationship among Zs[1], te[1] and X(te[1]), and tc[1] and X(tc[1]) on a coagulation reaction curve (curve made up of $X(i)$) is shown.

Further, a measurement time te[2] at a measurement point when $Z(i)$ for the first time reaches a value less than the predetermined second threshold Zs[2] ($Z(i)<Zs[2]$) (where $Zs[2]<Zs[1]$ is obtained) is detected. If necessary, acquisition of the $Z(i)$ is continued until $Z(i)<Zs[2]$ is satisfied. X in te[2] is X(te[2]). Next, a time tc[2] at a measurement point corresponding to X(i) having or approximating to the value of Q % of X(te[2]) is detected (where $tc[2]<te[2]$ is satisfied).

The above-determined te is a time point when $Z(i)$ reaches the threshold Zs, and represents a temporary coagulation end point. Meanwhile, the tc is a time point when the value of X reaches Q % of X at the temporary coagulation end point, and represents a temporary coagulation point. FIG. 4B is a conceptual diagram showing Zs[1] to Zs[3], and corresponding temporary coagulation end points te[1] to te[3], X(te[1]) to X(te[3]) at that time, and temporary coagulation points tc[1] to tc[3] on a reaction curve X. As shown in FIG. 4B, as the reaction curve comes closer to the plateau (the coagulation reaction comes closer to the termination), the increase in the te becomes larger while the increase in the X(te) gradually smaller. Meanwhile, as the coagulation reaction curve comes closer to the plateau, the tc also gradually increases, however, the change is smaller than that of the te.

1.2.3 Calculation of Tc

In the method of the present invention, by using the changes in the temporary coagulation end point te and temporary coagulation point tc with the progress of coagulation reaction as described above, a Tc calculation step of determining whether or not the temporary coagulation point tc is the true coagulation time Tc is conducted. That is, in the method of the present invention, an index for Tc calculation is acquired by using, for example, the parameters te, tc, and X(te) derived from the above-determined Zs (step S4).

Accordingly, in the method of the present invention, a measurement point when $Z(i)$ for the first time reaches a value less than the $k^{th}$ threshold Zs[k] ($Z(i)<Zs[k]$) (where $Zs[k]<Zs[k-1]$, and k an integer of 2 are satisfied) is detected. If necessary, acquisition of the $Z(i)$ is continued until $Z(i)<Zs[k]$ is satisfied. Next, parameters derived from Zs[k] (for example, te[k], tc[k], and X(te[k])), and parameters derived from the $k-1^{th}$ threshold Zs[k-1] (where $Zs[k]<Zs[k-1]$ is satisfied) (for example, te[k-1], tc[k-1], and X(te[k-1])), which are acquired before the above parameters, are acquired.

Preferably, the index is acquired on the basis of one or more of te[k], tc[k], and X(te[k]), and one or more of te[k−1], tc[k−1], and X(te[k−1]).

In the Tc calculation step, in a case where the index satisfies the predetermined criteria, the temporary coagulation point tc[k] or tc[k−1] is determined as the coagulation time Tc.

Accordingly, the acquisition of the index can be performed after the acquisition of te[2], tc[2], and X(te[2]) that are derived from the second threshold Zs[2]. Preferably, the first index can be acquired on the basis of te[1], tc[1], or X(te[1]) derived from Zs[1], and te[2], tc[2], or X(te[2]) derived from Zs[2] at k=2.

In one embodiment, the index is a difference between the X(te[k]) derived from the k$^{th}$ threshold Zs[k] and the X(te[k−1]) derived from the preceding threshold Zs[k−1] or a ratio of the X(te[k]) to the X(te[k−1]). Preferably, R[k] in accordance with the following equation (2) is used as the index for Tc calculation.

$$R[k] = X(te[k]) / X(te[k-1]) \qquad (2)$$

The R[k] may be expressed by ratio or by percentage. If the R[k] is a value of or a value smaller than the predetermined reference value Rs, the tc[k] or the tc[k−1] can be determined as the coagulation time Tc. At this time, the te[k] or the te[k−1] can be determined as the true coagulation end point.

In another embodiment, first, Δtc[k], Δte[k], and TR[k] are calculated in accordance with the following equations (3) to (5). The TR[k] is used as the index for Tc calculation.

$$\Delta tc[k] = tc[k] - tc[k-1] \qquad (3)$$
$$\Delta te[k] = \Delta te[k] - te[k-1] \qquad (4)$$
$$TR[k] = \Delta tc[k] / \Delta te[k] \qquad (5)$$

The TR[k] may be expressed by ratio or by percentage. If the TR[k] is a value of or a value smaller than the predetermined reference value TRs, the tc[k] or the tc[k−1] can be determined as the coagulation time Tc. At this time, the te[k] or the te[k−1] can be determined as the true coagulation end point.

The reference values Rs and TRs can be appropriately set so that the accuracy of Tc determined by the present invention is a desired value. It is preferable to adjust the Rs and TRs so that, for example, the Tc determined by the method of the present invention for various specimens is 90% or more, and preferably 95% or more of the actually measured coagulation time. The actually measured coagulation time can be estimated from the coagulation reaction end point of a visually measured coagulation reaction curve. Alternatively, the Tc obtained when Zs is close to 1 (for example, Zs=1.001) may be estimated as the actually measured coagulation time. For example, the Rs (%) is preferably 110% or less, and more preferably 105% or less, and the TRs (%) is preferably 15% or less, and more preferably 10% or less.

In a preferred embodiment, in a case where both of the above two criteria are satisfied, for example, when R[k] Rs, and further TR[k] TRs are satisfied, the tc[k] or the tc[k−1] can be determined as the coagulation time Tc.

Meanwhile, in a case where the index does not satisfy the predetermined criteria, the above procedure is repeated with k=k+1. This procedure is repeated while incrementing the k until an index that satisfies the criteria is obtained.

A specific example of the procedure for acquisition of an index and Tc determination will be described below. Preferably, first, an index for Tc calculation is calculated by using the parameter te[1], tc[1], or X(te[1]) relating to Zs[1], and the parameter te[2], tc[2], or X (te [2]) relating to Zs[2].

In one embodiment, the index is a difference between the X(te[1]) and the X(te[2]), or a ratio of the X(te[1]) to the X(te[2]). Preferably, R[2] in accordance with the following equation is used as the index for Tc calculation.

$$R[2](\%)=\{X(te[2])/X(te[1])\}(\%) \qquad (2)'$$

In a preferred embodiment, first, Δtc[2], Δte[2], and TR[2] are calculated in accordance with the following equations. The TR[2] is used as the index for Tc calculation.

$$\Delta tc[2] = tc[2] - tc[1] \qquad (3)'$$
$$\Delta te[2] = \Delta te[2] - te[1] \qquad (4)'$$
$$TR[2](\%) = \{\Delta tc[2] / \Delta te[2]\}(\%) \qquad (5)'$$

In a case where the index satisfies the predetermined criteria, the tc[1] or tc[2] is determined as the coagulation time Tc. Preferably, the tc[2] is determined as the Tc. For example, if the above R[2] is a value of or a value smaller than the predetermined reference value Rs, the tc[2] or the tc[1] is determined as the Tc. Further, for example, if the above TR[2] is a value of or a value smaller than the predetermined reference value TRs, the tc[2] or the tc[1] is determined as the Tc. Preferably, in a case where both of the above two criteria are satisfied, for example, when R[2]≤Rs, and further TR[2]≤TRs are satisfied, the tc[2] or the tc[1] is determined as the Tc.

Meanwhile, in a case where the index does not satisfy the predetermined criteria, for the third threshold Zs[3] (where Zs[3]<Zs[2]), te[3], tc[3], or X(te[3])) is determined similarly as in the above, and the index is calculated from te[3], tc[3], X(te[3]) and te[2], tc[2], or X(te[2]) by a similar procedure.

For example, in a case where R[2] is larger than Rs, and further TR[2] is larger than TRs, for the third threshold Zs[3], X(te[3]) is determined similarly as in the above, and then R[3] is calculated in accordance with the above equation (2), and/or te[3] and tc[3] are determined, and then TR[3] is calculated in accordance with the above equations (3) to (5).

If the calculated index satisfies the criteria, the tc[2] or the tc[3] is determined as the Tc. Preferably, when R[3]≤Rs and/or TR[3]≤TRs is(are) satisfied, the tc[3] or the tc[2] is determined as Tc.

In a case where the index does not satisfy the criteria, the same procedure is further repeated for the fourth threshold Zs[4] (where Zs[4]<Zs[3] is satisfied).

In this way, the same procedure is repeated for the N$^{th}$ threshold Zs[N] (where Zs[N]<Zs[N−1], and N≥2 are satisfied) until the Tc is determined while sequentially performing the measurement of coagulation reaction and the acquisition of X, Y, and Z in parallel. Finally, the tc[N] or the tc[N−1] is determined as Tc. In this regard, if the difference between the Zs[N] and the Zs[N−1] is set within an appropriate range, the tc[N] and tc(N−1) when R[N]≤Rs and/or TR[N]≤TRs is(are) satisfied show values relatively close to each other, and thus, even if tc[N] is selected or the tc(N−1) is selected for the Tc, there is no practical problem in clinical decision using Tc. However, from the viewpoint of enhancing the reliability of the calculation value of Tc, it is desirable to select the tc[N] for Tc.

The method of the present invention is basically an application of the percent method that has been conventionally used as a general calculation method for a blood coagulation time. In the percent method, the time point when the coagulation reaction progresses to Q % (50% as an example) of the termination of the reaction is determined as the coagulation time Tc. Accordingly, it is ideal also in the method of the present invention to calculate, as the coagulation time Tc, a time point when the coagulation reaction reaches Q % upon the integration ratio Z being 1 or a value close to 1 (when the blood coagulation reaction is almost terminated). If the calculation conditions are appropriate, te[k] is a time point before the sigmoid coagulation reaction curve comes closer to the plateau, and thus, the coagulation time Tc determined by the method of the present invention does not differ significantly from the ideal value. Further, in the percent method, in a case where a time point when the coagulation reaction is a ratio Co (45% or less or 55% or more as an example) away from 50% of the termination of the reaction is set as the coagulation time, the 50% coagulation time with Q %=50% is determined, and then the coagulation time at Co may be calculated on the basis of the same time point of the termination of the reaction.

1.2.4 Threshold Zs

As shown in FIG. 2, Z(i) comes closer to 1 as the coagulation reaction curve made up of X(i) comes closer to the plateau. Accordingly, Zs[k] is a value larger than 1. When the Zs[k] reaches the lowest value Zsmin set in advance, the repetition of the above procedure is terminated, and the tc[k] or the tc[k−1], preferably the tc[k], which is calculated on the basis of the Zs[k], is determined as the coagulation time Tc. The Zsmin may be larger than 1, and may be appropriately set depending on the measurement conditions (for example, a reagent, an analyzer, and an analysis item). For example, in a case of APTT measurement, Zsmin is preferably 1.0001 to 1.05, more preferably 1.0002 to 1.01, and further preferably 1.0005 to 1.002 (for example, 1.001).

Alternatively, when the integer k to be incremented reaches the maximum number N set in advance, the repetition of the above procedure is terminated, and the tc[N] or tc[N−1], preferably the tc[N], which is calculated on the basis of the Zs[N], is determined as the coagulation time Tc. From the viewpoint of the efficiency of coagulation time calculation, N is preferably 20 or less, more preferably 10 or less, and further preferably 8 or less.

The first threshold Zs[1] may be appropriately set depending on the measurement conditions (for example, a reagent, an analyzer, and an analysis item). For example, in a case of APTT measurement, the first threshold Zs[1] is preferably 1.100 or less, more preferably 1.080 or less, and further preferably 1.050 or less. For example, in the APTT measurement of a FVIII-deficient specimen, an integration ratio Z when the coagulation reaction rate reaches the maximum is often from 1.03 to 1.04, and thus, around 1.04 is selected for Zs[1].

The increment width of threshold Zs (difference between Zs[k−1] and Zs[k], ΔZs)) can be determined depending on, for example, Zs[1], Zsmin, the maximum number N of k, or the measurement frequency of coagulation reaction (sampling period), and from the viewpoint of the accuracy and efficiency of coagulation time calculation, the increment width is preferably in the range of 0.050 to 0.001, more preferably in the range of 0.020 to 0.002, and further preferably in the range of 0.010 to 0.005.

It is preferable that values of Zs[1], Zsmin, the maximum number N of k, and ΔZs are set so as to be in the appropriate ranges described above, respectively. For example, preferred Zsmin, ΔZs, and N are determined, and Zs[1] can be determined in accordance with the preferred Zsmin, ΔZs, and N. Alternatively, preferred Zs[1], Zsmin, and N are determined, and ΔZs can be determined in accordance with the preferred Zs[1], Zsmin, and N.

For example, in a case of Zsmin=1.001, k≤8, and ΔZs=0.005, Zs[1]=1.036. In this regard, examples of the combination of Zs[1], Zsmin, ΔZs, and the number of repetitions in the method of the present invention are not limited to the examples described above, and a person skilled in the art can appropriately set the adequate values.

1.2.5 Error Processing

In a case where the te[k] that satisfies Z(i)<Zs[k] is not found or the index does not satisfy the criteria through the repetition of the procedure as described above, the Tc calculation step is terminated incompletely without determining the Tc. In such a case, in the method of the present invention, the tc[k] acquired last may be determined as the Tc, or it can be considered that the Tc cannot be calculated. In any case, when the Tc has not been determined, a result that Tc is not normally determined can be acquired.

2. Illustrative Procedure for Tc Determination

Figure 5:
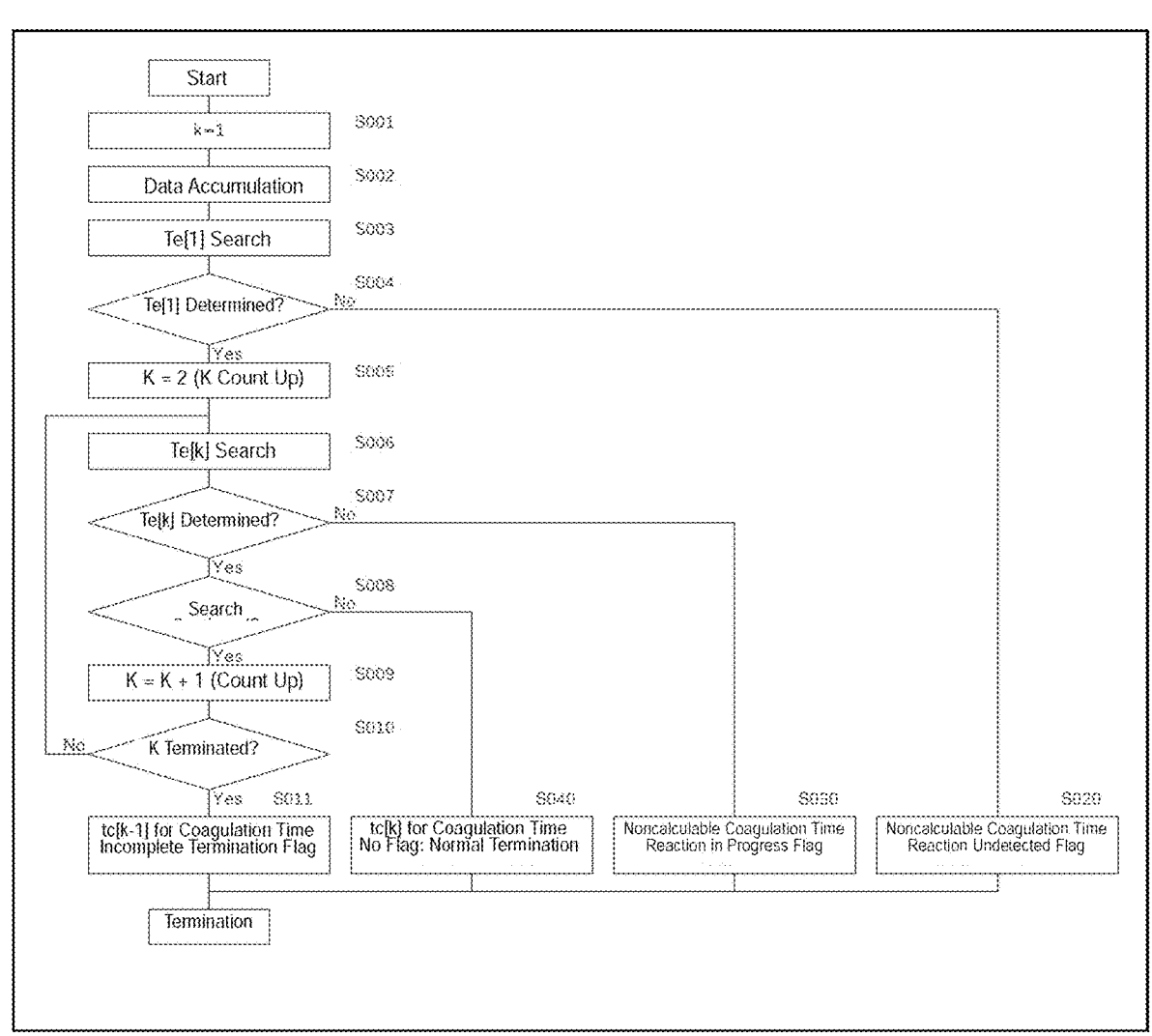
FIG. 5 shows a detailed flow of one embodiment of the blood coagulation time measurement method according to the present invention.

Hereinafter, an example of the more specific procedure for determining the coagulation time Tc according to the present invention will be described in more detail with reference to a detailed flow shown in FIG. 5. The procedure shown in FIG. 5 is an example, and ordinary changes, for example, a change of the order of calculations, can be made by a person skilled in the art.

S001: As shown in the following Table 1, Zs is set in advance from a high value to a low value stepwise, and an array Zs[k] is created so that each Zs can be sequentially selected by a variable k (counter). The k is an integer, and 1 is set as the initial value.

TABLE 1

| k | 1 | 2 | 3 | 4 | 5 | 6 | 7 | 8 |
|---|---|---|---|---|---|---|---|---|
| Zs[k] | 1.036 | 1.031 | 1.026 | 1.021 | 1.016 | 1.011 | 1.006 | 1.001 |

S002: After the number of data of the measured value P(i) (the i represents a measurement point number) relating to coagulation reaction exceeds the number of data (for example, 50) required for smoothing processing, initial fluctuation removal processing, and zero-point adjustment processing, acquisition of reaction X(i), differential value V(i), and integration ratio Z(i) is started.

S003: While continuing the acquisition of photometric data, X(i), V(i), and Z(i), a time te[1] at the earliest i at which Z(i)<Zs[1] is satisfied is searched after the calculation start point s. As described in 1.2.2 above, parameters such as X(te[1]), and tc[1] are determined from the searched te[1].

S004: In a case where a time te[1] at i at which Z(i)<Zs[1] is satisfied cannot be acquired in S003, the procedure branches out to S020 when the i reaches the upper limit value, and it is determined to be "reaction undetected", and the coagulation time is expressed as noncalculable". For example, in a case where the measurement (photometry) time is set to 360 seconds at 0.1-second intervals, the maximum number of measurement points is 3600, which is the upper limit value of the i. Meanwhile, in a case where the te[1] is acquired, the procedure branches out to S005.

S005: The k is counted up.

S006: In a case where the previous processing is S005, k=2 is obtained, and the previous processing is S010, the k is an integer of 3 or more. Next, while further continuing to acquire P(i), X(i), V(i), and Z(i), a time te[k] at i at which Z(i)<Zs[k] is satisfied is searched.

S007: In a case where the te[k] cannot be acquired in S006, the procedure branches out to S030 when the i reaches the upper limit value, and it is determined to be "reaction in progress", and the coagulation time is expressed as noncalculable. The upper limit value of the i is the same as that in S004. In a case where the te[k] was able to be acquired, the procedure branches out to S008.

S008: In a case where the te[k] has been able to be acquired in S006, parameters such as X(te[k]), and tc[k] are determined as described in 1.2.2 above. Parameters such as X(te[k−1]) and tc[k−1] are determined from the te[k−1] that satisfies Z(i)<Zs[k−1], and an index for Tc determination is calculated. Examples of the index include R[k] represented by the above equation (2), and TR[k] represented by the above equation (5). Either one of R[k] and TR[k] may be used as an index, but both of the R[k] and the TR[k] may be used as indexes.

Next, it is investigated whether or not the index satisfies the criteria. As the criteria, the following (a) or (b) can be mentioned, and preferably, it is required that both of the following (a) and (b) are satisfied.

$$R[k] \leq Rs \qquad \text{Criterion (a):}$$

$$TR[k] \leq TRs \qquad \text{Criterion (b):}$$

In a case where the above criteria are satisfied, the procedure branches out to S040, and in other cases, the procedure branches out to S009.

S009: In a case where neither one of the criteria (a) and (b) is satisfied in S008, the k is counted up.

S010: When the counted-up k exceeds the maximum value set in advance, the procedure branches out to S011. When the k is a value of the maximum value or less, the procedure branches out to S006, the k is counted up, and the search for a new te[k] is continued.

S011: Since the k has exceeded the maximum value without satisfying the criteria (a) and (b) are not satisfied in S008, the Tc determination procedure is incompletely terminated. In a case where the procedure proceeds to this step, Tc may or may not be output. In a case where the Tc is output, the tc acquired last (that is, tc[k−1]) is determined as the Tc. The Tc may be automatically output, or may be manually output by, for example, button operation.

S020: This is a case where the coagulation reaction measurement is terminated without finding the te[1] satisfying Z(i)<Zs[1], and the Tc is noncalculable. In a case where the procedure proceeds to this step, it can be determined that there is no coagulation reaction for some reason, and thus, a "reaction undetected" flag may be output.

S030: Since the te[k] satisfying Z(i)<Zs[k] was not found, Tc is noncalculable. In a case where the procedure proceeds to this step, it can be determined that the measurement was terminated in the middle of the coagulation reaction, and thus, a "reaction in progress" flag may be output.

S040: The coagulation end point has been confirmed, and tc[k−1] or tc[k] is output as Tc. Preferably, tc(k) is output as Tc. No flag, or a "normal termination" flag may be output.

3. Application to Other Coagulation Reaction Measurement Methods

The method of the present invention is basically a blood coagulation time measurement method using blood coagulation reaction measurement based on an amount of scattered light, and a person skilled in the art can apply the method of the present invention to other measurement methods, for example, a blood coagulation time measurement method using blood coagulation reaction measurement based on transmittance, or absorbance.

EXAMPLES

Hereinafter, the present invention will be described in more detail by way of Examples, however, the present invention is not limited to the following Examples.

Example 1

1. Method

Multiple mixed samples each obtained by mixing a blood specimen derived from a subject with coagulation reaction abnormality due to a blood coagulation factor (abnormal specimen) and a normal blood specimen (normal specimen) in different proportions, respectively, were subjected to measurement of a coagulation time in accordance with the method of the present invention.

1) Sample

As the abnormal specimen, Factor VIII Deficient Plasma (manufactured by George King Bio-Medical, Inc.) having a VIII factor (FVIII) concentration of 0.1% or less (hereinafter, referred to as "FVIII-deficient plasma") was used. As the normal specimen, normal pool plasma in which the FVIII concentration can be regarded as 100% (hereinafter, referred to as "normal plasma") was used. By changing the mixing ratio of the FVIII-deficient plasma to the normal plasma, mixed plasmas with FVIII concentrations of 50%, 25%, 10%, 5%, 2.5%, 1%, 0.75%, 0.5%, and 0.25% (samples 1 to 9 in that order) were respectively prepared. Further, only the FVIII-deficient plasma (with a FVIII concentration of 0.1% or less) was used as sample 10.

2) Reagent

As the reagent for measuring APTT, Coagpia APTT-N (manufactured by Sekisui Medical Co., Ltd.) was used. As the calcium chloride solution, a calcium chloride solution of Coagpia APTT-N (manufactured by Sekisui Medical Co., Ltd.) was used.

3) Coagulation Reaction Measurement

The coagulation reaction measurement was performed by using a blood coagulation automated analyzer, CP3000 (manufactured by Sekisui Medical Co., Ltd.) Into a cuvette (reaction vessel), 50 μL of a sample was aliquoted, and then heated at 37° C. for 45 seconds, next, 50 μL of a reagent for measuring APTT heated to around 37° C. was added into the cuvette, and after the lapse of 171 seconds, 50 μL of 25 mM calcium chloride solution was further added thereto to start coagulation reaction. The reaction was conducted while maintaining the temperature at around 37° C. In the measurement (photometry) of the coagulation reaction, the cuvette was irradiated with light having a wavelength of 660 nm using an LED light source, and the amount of scattered light of 90-degree side scattered light was measured at 0.1-second intervals. The maximum measurement time was set to 360 seconds (the number of data of 3600, and 0.1-second intervals).

4) Creation of Coagulation Reaction Curve

The photometric curve P was determined from the photometric data, a smoothing processing including noise removal was performed on the P, and then a zero-point adjustment for adjusting the amount of scattered light at the start point of photometry to be 0 was performed, and the reaction X was calculated.

5) Acquisition of Differential Value V and Integration Ratio Z

A primary differential value V, and an integration ratio Z in accordance with the following equation (1) were calculated from the reaction X.

$$Z(i) = \{X(i+1) + X(i+2) + \dots + X(i+m)\} / X(i-m) + \quad (1)$$

$$X(i-m+1) + \dots + X(i-1)\}$$

$$m = 20$$

The calculation of Z was started under the conditions that from X(i−m) to X(i−1) were all Xs or more. The Xs was set to 350.

6) Calculation Start Point

As the calculation start point s, a point when Z(i) exceeded a predetermined value and then became lower than the predetermined value was used. The predetermined value was set to 1.2.

7) Setting of Threshold Zs

The Zs[k] was set as shown in the following Table 2.

TABLE 2

| k | 1 | 2 | 3 | 4 | 5 | 6 | 7 | 8 |
|---|---|---|---|---|---|---|---|---|
| Zs[k] | 1.036 | 1.031 | 1.026 | 1.021 | 1.016 | 1.011 | 1.006 | 1.001 |

8) Parameter

Parameters were te[k], tc[k], X(te[k]), te[k−1], tc[k−1], and X(te[k−1]) (k=an integer of 2 to 8).

9) Index for Coagulation Time Tc Calculation $$\text{Index } (a): R[k](\%)( = X(te[k]) / X(te[k-1]) \times 100)$$

$$\text{Index } (b): TR[k](\%)( = \Delta C / \Delta E \times 100)$$

$$\Delta C = tc[k] - tc[k-1]$$

$$\Delta E = te[k] - te[k-1]$$

10) Calculation Process

The reaction X, the integration ratio Z, and, as needed, the differential value V were sequentially acquired from the photometric data, the parameters te[k], tc[k], X(te[k]), te[k−1], tc[k−1], and X(te[k−1]) were calculated by using Zs[k] shown in Table 1 after the calculation start point s, and further, the index (a): R[k] (%), and the index (b): TR[k] (%) were calculated. The tc[k] when the following criteria (a) and (b) were satisfied was taken as the coagulation time Tc. The above process was repeated while increasing the k by 1 up to 8 until the following criteria (a) and (b) were satisfied with the initial value k=1. In a case where the criteria were not satisfied with k=8, the tc[8] was taken as Tc.

$$R[k](\%) \leq Rs, Rs = 105\% \qquad \text{Criterion (a):}$$

$$TR[k](\%) \leq TRs, TRs = 10\% \qquad \text{Criterion (b):}$$

In this regard, in the present Example, and the following Examples, for the evaluation of the determined Tc, the coagulation reaction measurement was continued up to the maximum measurement time even after the Tc determination criteria were satisfied (the following criteria (a) and (b) both were satisfied), and parameters and indexes were acquired.

2. Evaluation of Tc Calculation Criteria

Figure 6:
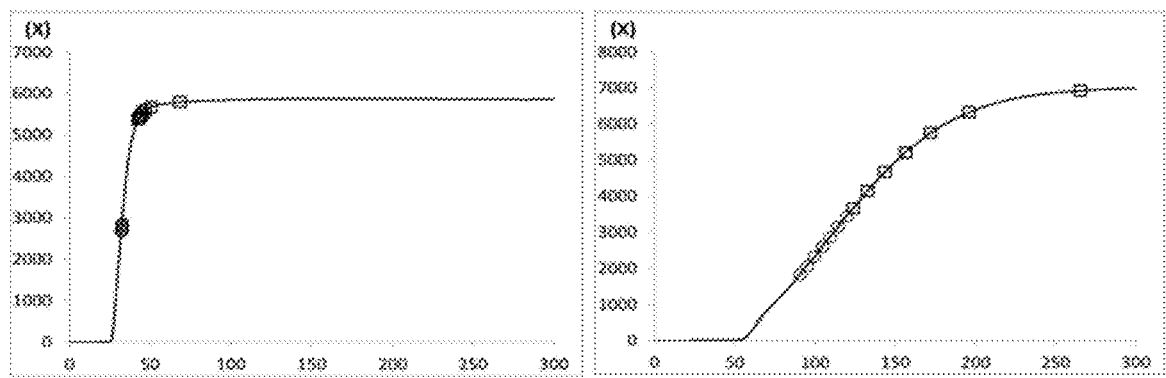
FIG. 6 shows reaction curves of X for sample 1 (left) and sample 10 (right).

1) Time Changes in Temporary Coagulation End Point to and Temporary Coagulation Point Tc FIG. 6 shows reaction curves of X in sample 1 (left, with a FVIII concentration of 50%) and sample 10 (right, with a FVIII concentration of 0.1% or less) to the measurement time. As for the markers on the curves, the white square indicates the temporary coagulation end point te[k], and the white circle indicates the temporary coagulation point tc[k] (k=2 to 8, and Zs[k]=1.031 to 1.001). In both of samples 1 and 10, the tc[2] and te[2] were the smallest, and the tc[8] and te[8] were the largest. In both of samples 1 and 10, the temporary coagulation end point te[8] (Zs[8]=1.001) was a value that was able to be visually determined to be the true coagulation reaction termination point. The values of tc[k] were almost the same in sample 1, while the values were different in sample 10.

Figure 7:
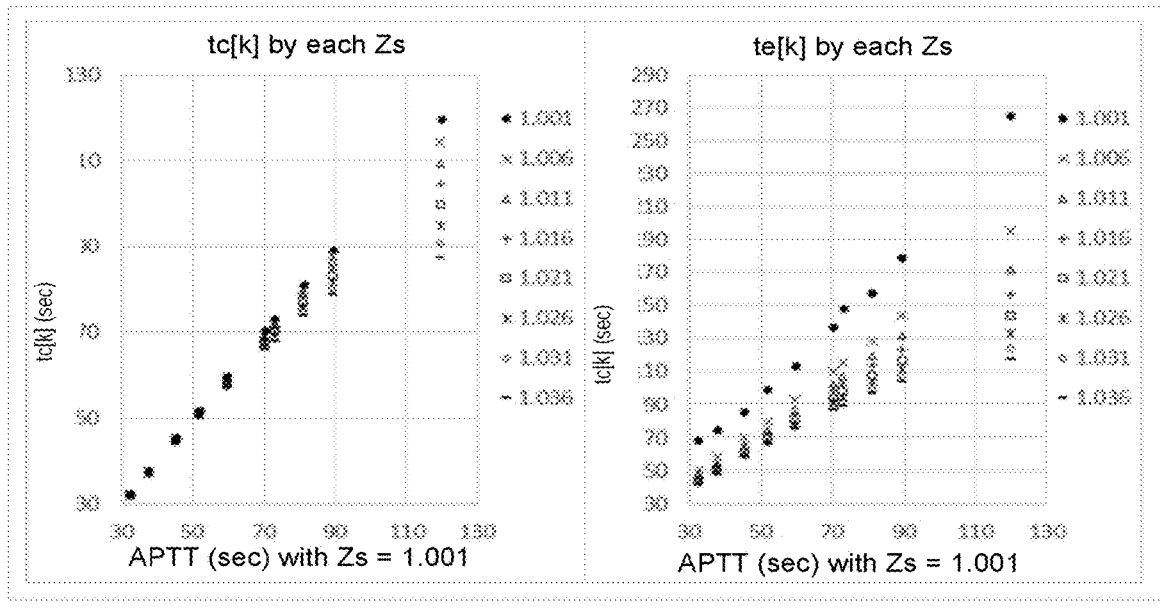
FIG. 7 shows tc[k] (left) and te[k] (right) with different Zs[k].

The time point when Z(i)<Zs[8] (=1.001) was satisfied was taken as the coagulation end point, and the time point when X was 50% of the coagulation end point was taken as APTT. FIG. 7 shows plots of tc[k] (left) and te[k] (right) to APTT at Zs[k] (k=1 to 8, and Zs[k]=1.036 to 1.001) in samples 1 to 10. The longer the APTT was, the wider the distribution width of the temporary coagulation point tc[k] was. A similar tendency was confirmed also for the temporary coagulation end point te[k]. However, the latest point te[8] was at a position distant from the other points.

2) Tc Determination Criteria for Index (a)

Figure 8:
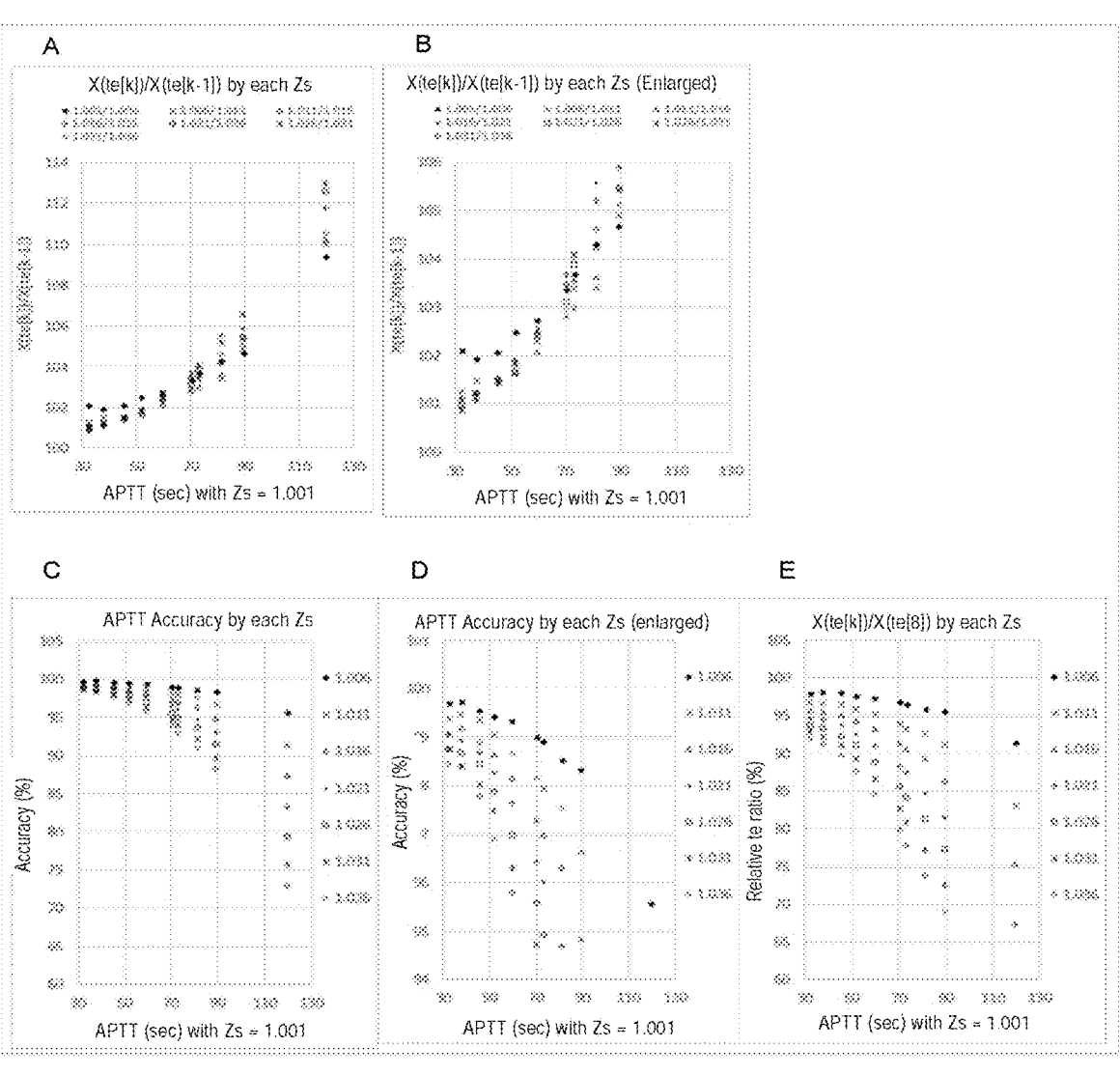
FIG. 8 shows A and B: plots of R[k] (%) to APTT and the enlarged view, C and D: plots showing the accuracy of Tc calculation by R[k] (%) and the enlarged view, and E: plots of X(te[k])/X(te[8]) with different Zs[k].

FIG. 8A and FIG. 8B show plots (A) of the index (a): R[k] (%) determined for samples 1 to 10 to APTT, and an enlarged view (B) thereof. The distribution of R[k] was different depending on the APTT even if the R[k] was derived from the same Zs value. It was found from FIG. 8B that by setting the reference value Rs for Tc determination to 105%, R[k] Rs was satisfied in around 96% of cases, and the coagulation time Tc (APTT) could be calculated accurately.

FIG. 8C and FIG. 8D show plots (C) indicating the accuracy of Tc calculation by R[k] (%) from samples 1 to 10 by each corresponding Zs[k], and an enlarged view (D) thereof. The vertical axis represents a relative Tc calculation value in Zs[1] to Zs[7] when the Tc calculation value with Zs=1.001 (Zs[8]) in each sample is taken as 100%, and represents the accuracy (%) of the calculation value. The Zs value having an accuracy of 96% or more does not exist in sample 10 (APTT=around 130 seconds) (does not reach 96% even at Zs[7]=1.006), and exists at Zs[7]=1.006 and Zs[6]=1.011 in sample 9 (APTT=around 90 seconds). FIG. 8E shows plots indicating the X(te[k])/X(te[8]) (%) by each corresponding Zs[k]. The vertical axis represents a relative value of X(te[1]) to X(te[7]) at Zs[1] to Zs[7] when X(te[8]) with Zs=1.001 (Zs[8]) in each sample was taken as 100%, and represents the relative height (%) of the reaction curve X. The relative height had a distribution depending on the size of APTT. When comparing with FIG. 8A, it was found that as the relative height of the reaction curve came closer to 100%, the R[k] reduced also toward 100%.

From the above, when the coagulation time Tc is determined, it has been shown that [R[k] (%) 105%] can be set as a criterion indicating that the relative height of the reaction curve has reached 90% (that is, the coagulation reaction is in the terminating stage).

3) Tc Determination Criteria for Index (b)

Figure 9:
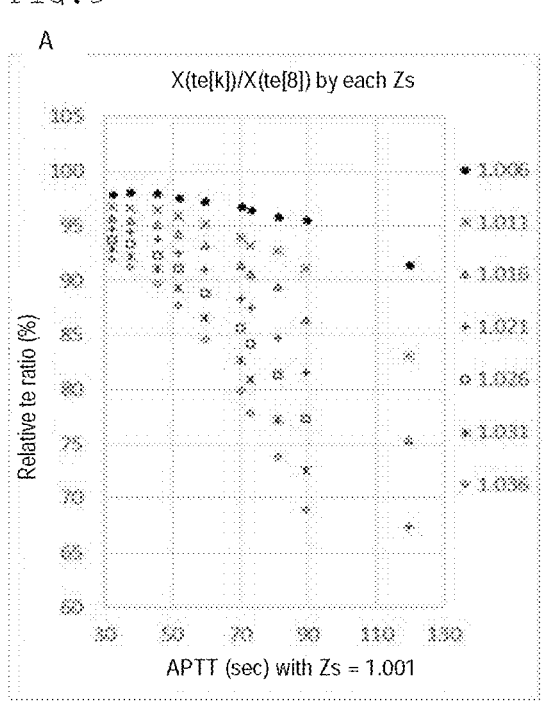
FIG. 9 shows A: plots of X(te[k])/X(te[8]) with different Zs[k], and B to D: plots of TR[k] (ΔC/ΔE) (%), ΔE, and ΔC to APTT.
Figure 9:
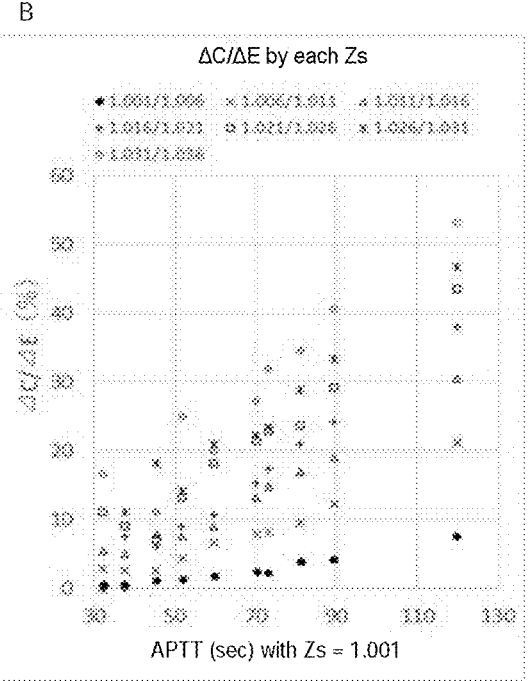
Figure 9:
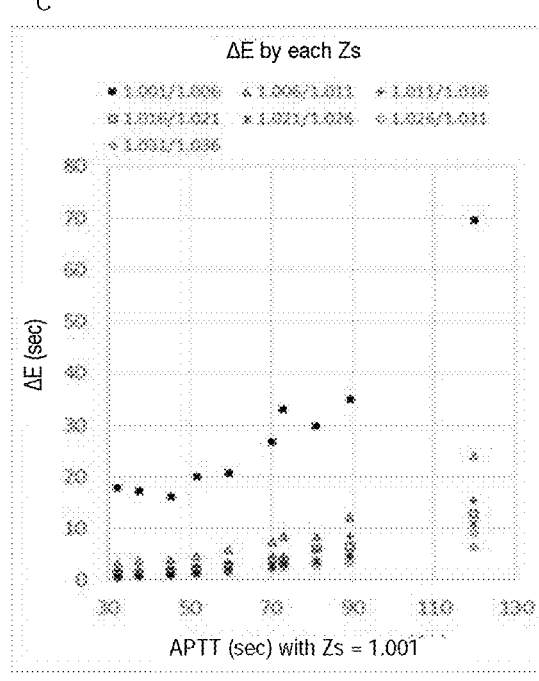
Figure 9:
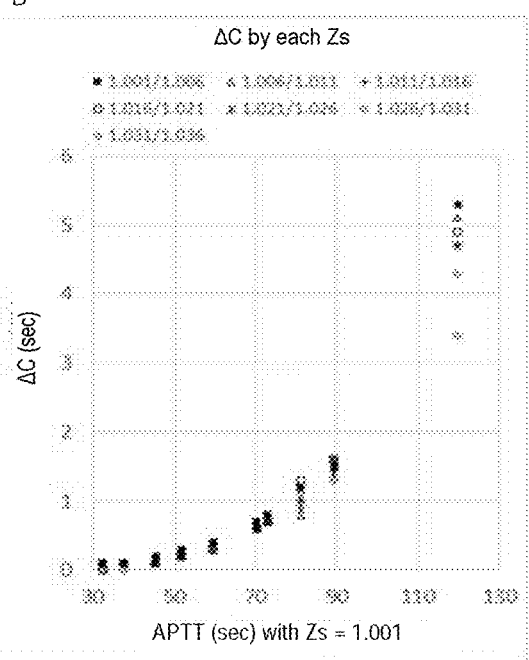

FIG. 9A shows plots indicating the X(te[k])/X(te[8]) (%) by each corresponding Zs[k] (the same as FIG. 8E), and FIG. 9B to FIG. 9D show plots of index (b): TR[k] (=ΔC/ΔE) (%), ΔE, and ΔC to APTT, respectively. ΔE and ΔC tended to increase depending on the APTT value, and the change in the amount was larger in ΔE than in ΔC (FIG. 9C and FIG. 9D). As a result, as shown in FIG. 9B, the TR[k] (=ΔC/ΔE), which is a ratio of the changes in the amounts of the two, also increased depending on the APTT. The distribution of TR[k] to APTT showed the same behavior as that when the vertical axis of FIG. 9A (X(te[k])) was reversed. Accordingly, it has been shown that TR[k] indirectly reflects the relative height of the reaction curve at X(te[k]).

3. Tc Determination

The parameters and indexes acquired in samples 1 to 10 are shown in Tables 3 to 6. The Tc calculation process was terminated without reaching the maximum measurement time in all of the samples. Columns of parameters and indexes after Tc was determined are each shown with a diagonal line. An asterisk shows that the index satisfied the criterion (a) or (b).

TABLE 3

| | | | | Sample 1 | | | | |
|---|---|---|---|---|---|---|---|---|
| k | 1 | 2 | 3 | 4 | 5 | 6 | 7 | 8 |
| Zs[k] | 1.036 | 1.031 | 1.026 | 1.021 | 1.016 | 1.011 | 1.006 | 1.001 |
| te[k] | 41.9 | 42.5 | 43.2 | — | — | — | — | — |
| tc[k] | 31.8 | 31.9 | 31.9 | — | — | — | — | — |
| X(te[k]) | 5322 | 5372 | 5418 | — | — | — | — | — |
| R[k] | — | 100.9* | 100.9* | — | — | — | — | — |
| te[k]-te[k-1] | — | 0.6 | 0.7 | — | — | — | — | — |
| tc[k]-tc[k-1] | — | 0.1 | 0 | — | — | — | — | — |
| TR[k] | — | 16.7 | 0.0* | — | — | — | — | — |

| | | | | Sample 2 | | | | |
|---|---|---|---|---|---|---|---|---|
| k | 1 | 2 | 3 | 4 | 5 | 6 | 7 | 8 |
| Zs[k] | 1.036 | 1.031 | 1.026 | 1.021 | 1.016 | 1.011 | 1.006 | 1.001 |
| te[k] | 48.2 | 48.9 | 49.8 | 50.9 | — | — | — | — |
| tc[k] | 37.0 | 37.0 | 37.1 | 37.2 | — | — | — | — |
| X(te[k]) | 5307 | 5364 | 5427 | 5493 | — | — | — | — |
| R[k] | — | 101.1* | 101.2* | 101.2* | — | — | — | — |
| te[k]-te[k-1] | — | 0.7 | 0.9 | 1.1 | — | — | — | — |
| tc[k]-tc[k-1] | — | 0 | 0.1 | 0.1 | — | — | — | — |
| TR[k] | — | 0.0* | 11.1 | 9.1* | — | — | — | — |

| | | | | Sample 3 | | | | |
|---|---|---|---|---|---|---|---|---|
| k | 1 | 2 | 3 | 4 | 5 | 6 | 7 | 8 |
| Zs[k] | 1.036 | 1.031 | 1.026 | 1.021 | 1.016 | 1.011 | 1.006 | 1.001 |
| te[k] | 58.0 | 58.9 | 60.0 | 61.4 | — | — | — | — |
| tc[k] | 44.4 | 44.5 | 44.7 | 44.8 | — | — | — | — |
| X(te[k]) | 5541 | 5619 | 5701 | 5787 | — | — | — | — |
| R[k] | — | 101.4* | 101.5* | 101.5* | — | — | — | — |
| te[k]-te[k-1] | — | 0.9 | 1.1 | 1.4 | — | — | — | — |
| tc[k]-tc[k-1] | — | 0.1 | 0.2 | 0.1 | — | — | — | — |
| TR[k] | — | 11.1 | 18.2 | 7.1* | — | — | — | — |

TABLE 4

| | | | | Sample 4 | | | | |
|---|---|---|---|---|---|---|---|---|
| k | 1 | 2 | 3 | 4 | 5 | 6 | 7 | 8 |
| Zs[k] | 1.036 | 1.031 | 1.026 | 1.021 | 1.016 | 1.011 | 1.006 | 1.001 |
| te[k] | 65.8 | 67.0 | 68.4 | 69.9 | 72.1 | — | — | — |
| tc[k] | 50.2 | 50.5 | 50.7 | 50.9 | 51.1 | — | — | — |
| X(te[k]) | 5580 | 5686 | 5792 | 5888 | 5999 | — | — | — |
| R[k] | — | 101.9* | 101.9* | 101.7* | 101.9* | — | — | — |
| te[k]-te[k-1] | — | 1.2 | 1.4 | 1.5 | 2.2 | — | — | — |
| tc[k]-tc[k-1] | — | 0.3 | 0.2 | 0.2 | 0.2 | — | — | — |
| TR[k] | — | 25.0 | 14.3 | 13.3 | 9.1* | — | — | — |

TABLE 4-continued

| | | | | Sample 5 | | | | |
|---|---|---|---|---|---|---|---|---|
| k | 1 | 2 | 3 | 4 | 5 | 6 | 7 | 8 |
| Zs[k] | 1.036 | 1.031 | 1.026 | 1.021 | 1.016 | 1.011 | 1.006 | 1.001 |
| te[k] | 75.1 | 76.6 | 78.5 | 80.7 | 83.5 | 86.8 | — | — |
| tc[k] | 57.1 | 57.4 | 57.8 | 58.2 | 58.5 | 58.5 | — | — |
| X(te[k]) | 5391 | 5518 | 5659 | 5797 | 5939 | 6063 | — | — |
| R[k] | — | 102.4* | 102.6* | 102.4* | 102.4* | 102.1* | — | — |
| te[k]-te[k-1] | — | 1.5 | 1.9 | 2.2 | 2.8 | 3.3 | — | — |
| tc[k]-tc[k-1] | — | 0.3 | 0.4 | 0.4 | 0.3 | 0.3 | — | — |
| TR[k] | — | 20.0 | 21.1 | 18.2 | 10.7 | 9.1* | — | — |

| | | | | Sample 6 | | | | |
|---|---|---|---|---|---|---|---|---|
| k | 1 | 2 | 3 | 4 | 5 | 6 | 7 | 8 |
| Zs[k] | 1.036 | 1.031 | 1.026 | 1.021 | 1.016 | 1.011 | 1.006 | 1.001 |
| te[k] | 86.5 | 88.7 | 91.4 | 94.2 | 98.1 | 102.6 | 110.1 | — |
| tc[k] | 65.9 | 66.5 | 67.1 | 67.7 | 68.3 | 68.9 | 69.5 | — |
| X(te[k]) | 5362 | 5549 | 5753 | 5932 | 6136 | 6310 | 6497 | — |
| R[k] | — | 103.5* | 103.7* | 103.1* | 103.4* | 102.8* | 103.0* | — |
| te[k]-te[k-1] | — | 2.2 | 2.7 | 2.8 | 3.9 | 4.5 | 7.5 | — |
| tc[k]-tc[k-1] | — | 0.6 | 0.6 | 0.6 | 0.6 | 0.6 | 0.6 | — |
| TR[k] | — | 27.3 | 22.2 | 21.4 | 15.4 | 13.3 | 8.0* | — |

TABLE 5

| | | | | Sample 7 | | | | |
|---|---|---|---|---|---|---|---|---|
| k | 1 | 2 | 3 | 4 | 5 | 6 | 7 | 8 |
| Zs[k] | 1.036 | 1.031 | 1.026 | 1.021 | 1.016 | 1.011 | 1.006 | 1.001 |
| te[k] | 89.1 | 91.6 | 94.6 | 98.1 | 102.1 | 106.8 | 115.2 | — |
| tc[k] | 67.8 | 68.6 | 69.3 | 70.1 | 70.8 | 71.5 | 72.2 | — |
| X(te[k]) | 4969 | 5167 | 5378 | 5587 | 5785 | 5958 | 6161 | — |
| R[k] | — | 104.0* | 104.1* | 103.9* | 103.5* | 103.0* | 103.4* | — |
| te[k]-te[k-1] | — | 2.5 | 3 | 3.5 | 4 | 4.7 | 8.4 | — |
| tc[k]-tc[k-1] | — | 0.8 | 0.7 | 0.8 | 0.7 | 0.7 | 0.7 | — |
| TR[k] | — | 32.0 | 23.3 | 22.9 | 17.5 | 14.9 | 8.3* | — |

| | | | | Sample 8 | | | | |
|---|---|---|---|---|---|---|---|---|
| k | 1 | 2 | 3 | 4 | 5 | 6 | 7 | 8 |
| Zs[k] | 1.036 | 1.031 | 1.026 | 1.021 | 1.016 | 1.011 | 1.006 | 1.001 |
| te[k] | 96.9 | 99.8 | 103.6 | 107.4 | 113.6 | 119.5 | 127.9 | — |
| tc[k] | 73.8 | 74.8 | 75.9 | 76.8 | 78.1 | 79.1 | 79.9 | — |
| X(te[k]) | 4777 | 4998 | 5258 | 5482 | 5787 | 5998 | 6202 | — |
| R[k] | — | 104.6* | 105.2 | 104.3* | 105.6 | 103.6* | 103.4* | — |
| te[k]-te[k-1] | — | 2.9 | 3.8 | 3.8 | 6.2 | 5.9 | 8.4 | — |
| tc[k]-tc[k-1] | — | 1 | 1.1 | 0.9 | 1.3 | 1 | 0.8 | — |
| TR[k] | — | 34.5 | 28.9 | 23.7 | 21.0 | 16.9 | 9.5* | — |

| | | | | Sample 9 | | | | |
|---|---|---|---|---|---|---|---|---|
| k | 1 | 2 | 3 | 4 | 5 | 6 | 7 | 8 |
| Zs[k] | 1.036 | 1.031 | 1.026 | 1.021 | 1.016 | 1.011 | 1.006 | 1.001 |
| te[k] | 103.9 | 107.1 | 111.9 | 116.7 | 123.3 | 131.7 | 143.9 | 178.9 |
| tc[k] | 78.8 | 20.1 | 81.7 | 83.1 | 84.7 | 86.3 | 87.8 | 89.3 |
| X(te[k]) | 4711 | 4952 | 5278 | 5567 | 5895 | 6216 | 6520 | 6825 |
| R[k] | — | 105.1 | 106.6 | 105.5 | 105.9 | 105.4 | 104.9* | 104.7* |
| te[k]-te[k-1] | — | 3.2 | 4.8 | 4.8 | 6.6 | 8.4 | 12.2 | 35 |
| tc[k]-tc[k-1] | — | 1.3 | 1.6 | 1.4 | 1.6 | 1.6 | 1.5 | 1.5 |
| TR[k] | — | 40.6 | 33.3 | 29.2 | 24.2 | 19.0 | 12.3 | 4.3* |

TABLE 6

| k | 1 | 2 | 3 | 4 | 5 | 6 | 7 | 8 |
|---|---|---|---|---|---|---|---|---|
| | | | | Sample 10 | | | | |
| Zs[k] | 1.036 | 1.031 | 1.026 | 1.021 | 1.016 | 1.011 | 1.006 | 1.001 |
| te[k] | 117.2 | 123.6 | 132.8 | 143.6 | 156.5 | 171.9 | 196.0 | 265.5 |
| tc[k] | 87.3 | 90.7 | 95.0 | 99.7 | 104.6 | 109.3 | 114.4 | 119.7 |
| X(te[k]) | 3313 | 3662 | 4138 | 4660 | 5209 | 5743 | 6319 | 6914 |
| R[k] | — | 110.5 | 113.0 | 112.6 | 111.8 | 110.3 | 110.0 | 109.4 |
| te[k]-te[k-1] | — | 6.4 | 9.2 | 10.8 | 12.9 | 15.4 | 24.1 | 69.5 |
| tc[k]-tc[k-1] | — | 3.4 | 4.3 | 4.7 | 4.9 | 4.7 | 5.1 | 5.3 |
| TR[k] | — | 53.1 | 46.7 | 43.5 | 38.0 | 30.5 | 21.2 | 7.6* |

Figure 10:
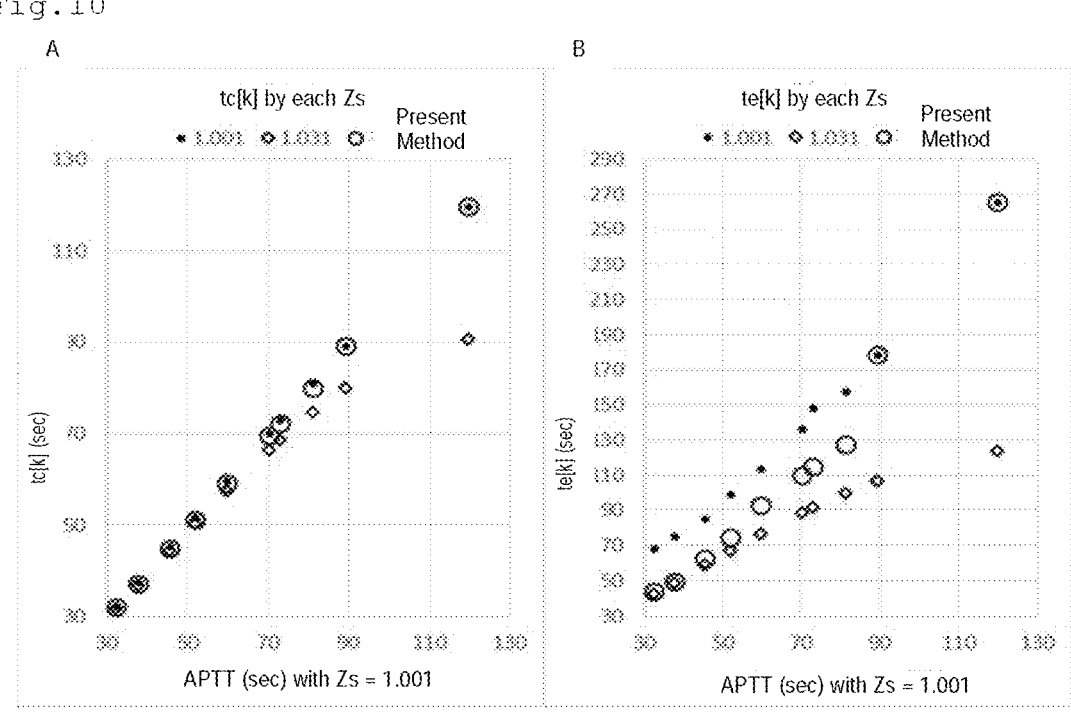
FIG. 10 shows A and B: tc[k] and te[k] calculated from samples 1 to 10, where the present method: the value when Tc is determined, the value with 1.001: Zs=1.001, and the value with 1.031: Zs=1.031, and C and D: the difference in tc[k] and te[k] between the present method or Zs=1.031 and Zs=1.001.
Figure 10:
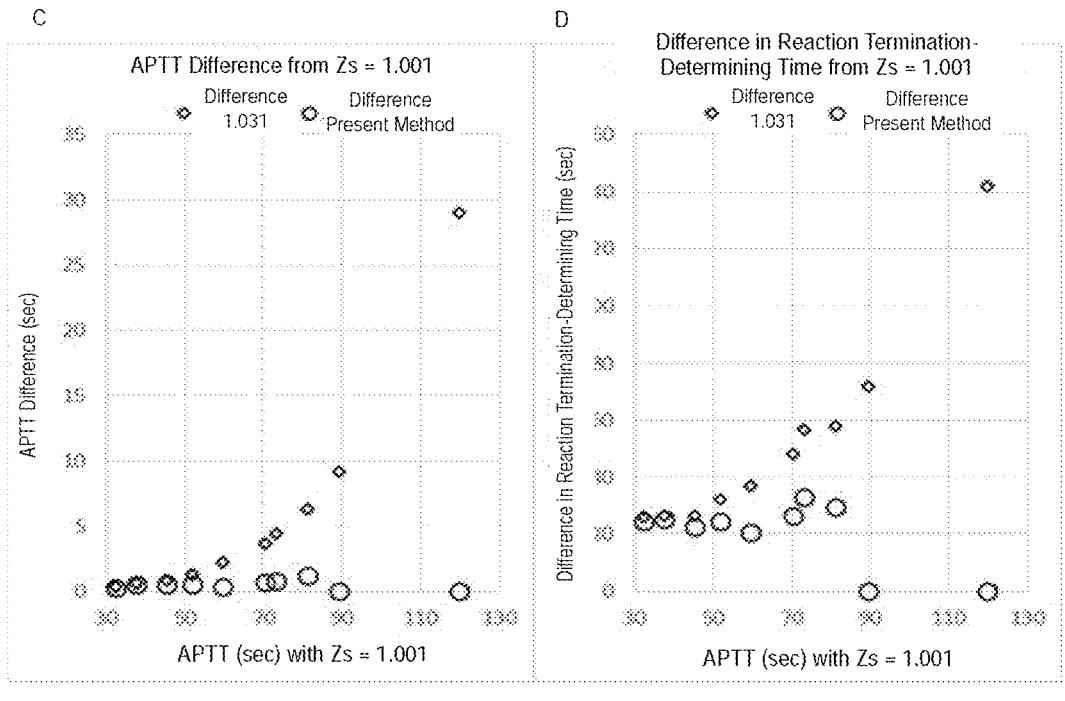

In FIG. 10A and FIG. 10B, the temporary coagulation point tc[k] (A) and temporary coagulation end point te[k] (B) when the coagulation time Tc was determined were plotted to APTT (the present method in the diagram). In the diagram, tc[k] and te[k] when Zs=1.001 (k=8) were plotted as a control, and tc[k] and te[k] when Zs=1.031 (k=2) were also plotted as a comparative example. Further, a difference obtained by subtracting each value of tc[k] and te[k] in the present method or Comparative Example from the value in the control (Zs=1.001, and k=8) is shown in FIG. 10C and FIG. 10D.

The tc[k] (=determined Tc) when Tc was determined by the present method overlapped with the tc[k] (almost equal to APTT) in the control. The difference in tc[k] between the present method and the control was within 1 second. In addition, the te[k] in the present method was close to that in the comparative example when the APTT was short, but overlapped with that in the control after 90 seconds of the APTT. The te[k] was 33 seconds at the shortest (right diagram). This indicates that in a case where the APTT is less than 90 seconds, the coagulation reaction measurement time required to obtain Tc by the present method is shorter by around 20 seconds to around 30 seconds than that of the control. Meanwhile, the difference in tc[k] (=determined Tc) between the comparative example and the control is within 1 second when the APTT is up to 50 seconds, but increases with the prolongation of the APTT and is 29 seconds at the maximum, and the difference in te[k] was 26 seconds at the minimum and 142 seconds at the maximum. That is, in the comparative example, the coagulation reaction measurement time was shorter than that of the control, however, the coagulation time equal to that of the control was obtained in a case where the APTT was less than 50 seconds, and the coagulation time was calculated to be shorter than that of the control when the APTT exceeded 50 seconds. From the above, it has been shown that both of the accurate calculation of the coagulation time and the shortening of the measurement time can be achieved by the method of the present invention.

Example 2

As the specimen, by using Factor XII Deficient Plasma (manufactured by George King Bio-Medical, Inc.) having a XII factor concentration of 0.1% or less (hereinafter, referred to as "FXII-deficient plasma", with a FXII concentration of 0%), and normal pool plasma in which the FXII concentration can be regarded as 100° (hereinafter, referred to as "normal plasma"), a mixed plasma (sample 11) having an FXII concentration of 0.25% with a mixing ratio of the FXII-deficient plasma to the normal plasma of 1:39 was prepared.

Figure 11:
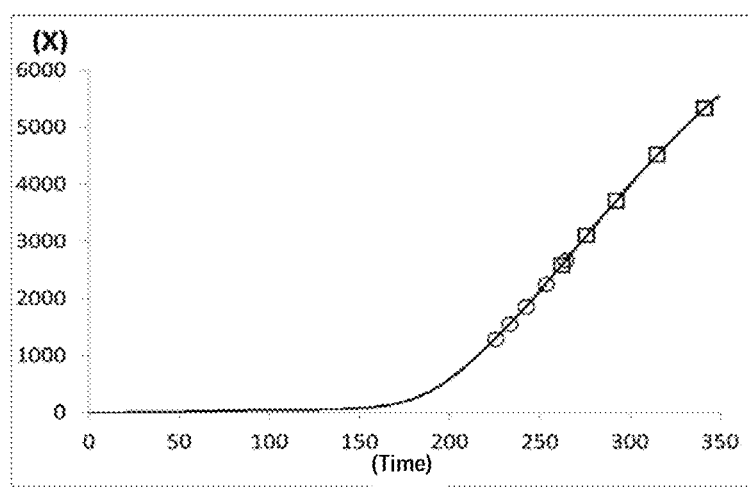
FIG. 11 shows a reaction curve of the APTT prolongation specimen of which the reaction does not terminate within the measurement time, and a table showing the parameters and indexes acquired.

For the prepared sample 11, Tc satisfying the criteria (a) and (b) was searched by a similar procedure as in 1.10) of Example 1. However, in this sample, although te[k] and tc[k] were obtained up to k=6 (Zs=1.011), the measurement time reached the maximum before the acquisition of k=7 (Zs=1.006), and thus the Tc calculation process was terminated. As a result, in the present Example, the coagulation time Tc was not output, but a flag indicating "reaction in progress" was output. The reaction curve X (te[k] and te[k] are shown) for sample 11, and the calculated parameters and indexes are shown in FIG. 11.

Example 3

Figure 12:
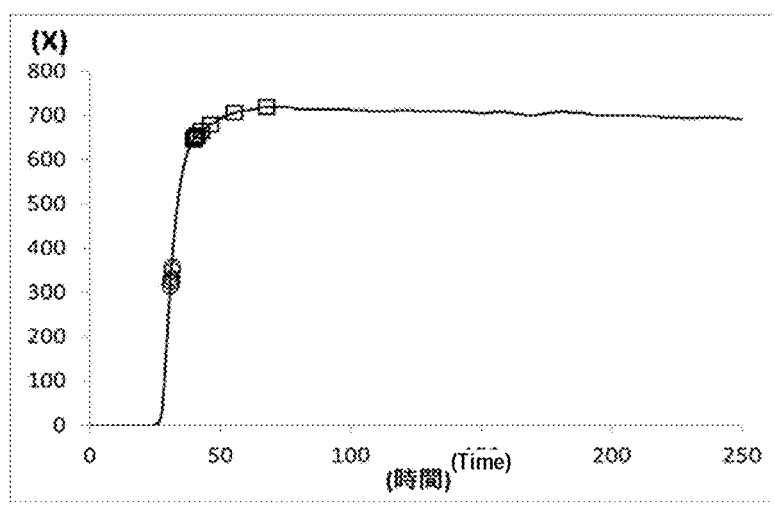
FIG. 12 shows a reaction curve of a low fibrinogen sample, and a table showing the parameters and indexes acquired.

For a specimen (sample 12) with a low fibrinogen concentration (62 mg/dL), Tc satisfying the criteria (a) and (b) was searched by a similar procedure as in 1.10) of Example 1. The criteria (a) and (b) were satisfied at k=2 (Zs=1.031), and the coagulation time Tc was determined to be 30.9 seconds. The reaction curve X (te[k] and tc[k] of k=1 to 8 are shown) for sample 12, and the calculated parameters and indexes are shown in FIG. 12. A gray column in the table of FIG. 12 shows that the index satisfied the criterion (a) or (b). The maximum value of the coagulation reaction in FIG. 12 was around 1/8 when comparing with that on the left in FIG. 6 with a normal level of the fibrinogen concentration, however, it has been able to be confirmed that the coagulation time Tc can be calculated by the method of the present invention even in a sample having such a low fibrinogen concentration.

Example 4

The conditions of the calculation start point s of Tc calculation were evaluated. As the sample, a specimen (sample 13) with a reaction curve of a gradual increase continued in the initial reaction stage was used. The calculation start point s was determined in accordance with the following conditions, Tc satisfying the criteria (a) and (b) was searched by a similar procedure as in 1.10) of Example 1.

Condition 1 (the same as that in the conventional technique): After the integration ratio Z exceeded the peak, that is, after the Z exceeded a predetermined value, a point when the Z became lower than the predetermined value was taken as the calculation start point s. The predetermined value of Z was set to 1.2.

Condition 2: When the number of measurement points between two points when V(i)=Vs was satisfied across the peak exceeded Ws, a later point of the measurement points that satisfy V(i)=Vs was set as the calculation start point s (see FIG. 3). The Vs was set to 90% Vmax, and the Ws was set to 10 (1 second).

Condition 3: The same as Condition 2, except that the Vs was set to 50% Vmax and the Ws was set to 10 (1 second).

Figure 13:
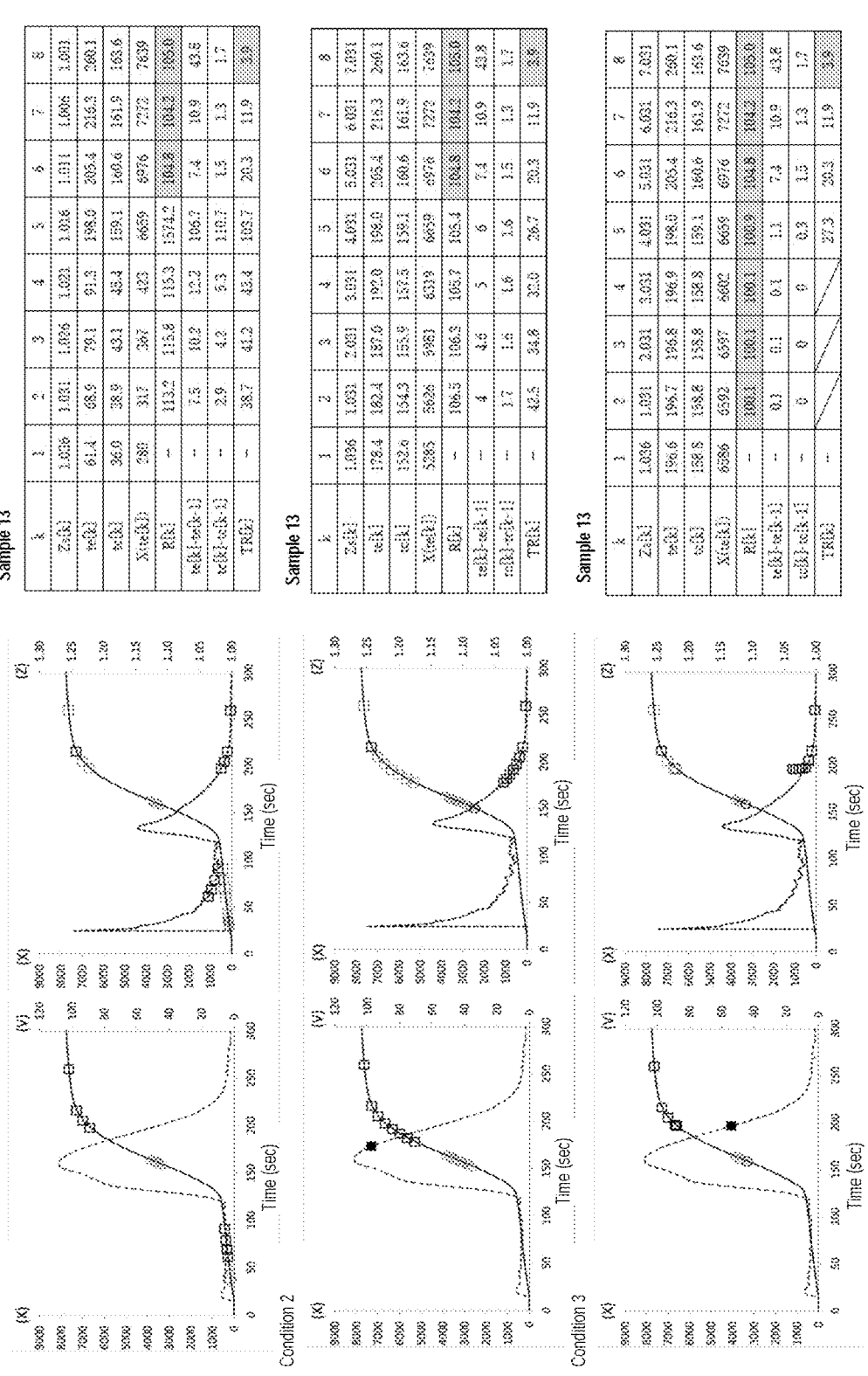
FIG. 13 shows influence of the calculation start point s detected under different conditions 1 to 3 on the parameters for Tc calculation.

FIG. 13 shows the parameters and indexes acquired under each of Conditions 1 to 3. The left diagrams show the reaction curve X and the differential value V, and the right diagrams show the X and the integration ratio Z. As for the markers in the diagrams, the white square indicates Te[k], and the white circle indicates Tc[k]. The right side shows tables of the parameters and indexes. A gray column in the tables shows that the index satisfied the criterion (a) or (b).

Under Condition 1, since the Z became lower than the predetermined value in gradually increasing part of the reaction curve X in the initial reaction stage, the Tc calculation was started before V(i) reached the maximum, and Te[k] and Tc[k] with k=1 to 4 were obtained. However, the Tc calculation process proceeded without satisfying the criteria (a) and (b), and finally Tc of 163.6 seconds was determined with k=8 (Zs=1.001).

Under Conditions 2 and 3, the Tc calculation was started after the V(i) exceeded the peak. The black square in the diagram is the calculation start point s. Under both Conditions 2 and 3, the criteria (a) and (b) were satisfied with k=8 (Zs=1.001), and Tc of 163.6 seconds was determined. However, under Condition 3, the Te[k] with k=1 to 4 were close to each other, and thus, the index with k=1 to 4 was processed so as not to be adopted in the Tc calculation.

The invention claimed is:

1. A blood coagulation time measurement method, comprising:

[1] acquiring reaction X(i) through smoothing and zero-point adjustment of a measured value P(i) for coagulation reaction of a blood specimen;

[2] acquiring an integration ratio Z(i) of the reaction X(i), wherein the Z(i) is a ratio of an integrated value of X in a first measurement section to an integrated value of X in a second measurement section adjacent to the first measurement section;

[3] calculating parameters te[k], X(te[k]), tc[k], te[k−1], X(te[k−1]), and tc[k−1], wherein, k is an integer of 2 or more, te[k] and te[k−1] are a measurement time at i satisfying Z(i)<Zs[k] and a measurement time at i satisfying Z(i)<Zs[k−1], respectively, X(te[k]) and X(te[k−1]) are reactions X at te[k] and te[k−1], respectively, tc[k] and tc[k−1] are a measurement time at i satisfying X(i)={X(te[k])×Q %} and a measurement time at i satisfying {X(te[k−1])×Q %}, respectively, and $1 < Q < 100;$

[4] calculating at least one of an index R[k] and an index TR[k], wherein, $$R[k] = X(te[k]) / X(te[k-1]) \tag{2}$$

$$TR[k] = \Delta tc[k] / \Delta te[k] \tag{5}$$

$$\Delta tc[k] = tc[k] - tc[k-1] \tag{3}$$

$$\Delta te[k] = \Delta te[k] - te[k-1]; \text{ and} \tag{4}$$

[5] determining the tc[k] or the tc[k−1] as a coagulation time Tc in a case where at least one of R[k] and TR[k] satisfy a predetermined condition, wherein Zs[k]<Zs[k−1] is satisfied, Zs[k] is greater than 1, and Zs[1] is 1.100 or less.

2. The method according to claim 1, wherein the steps [3] to [5] are repeated with k=k+1 in a case where the R[k] or TR[k] does not satisfy the predetermined condition in the step [5].

3. The method according to claim 2, further comprising acquiring a result that Tc is not normally determined when Tc is not determined through the repetition of the steps [3] to [5].

4. The method according to claim 1, wherein k is 10 or less.

5. The method according to claim 1, wherein a difference between Zs[k−1] and Zs[k] is from 0.050 to 0.001.

6. The method according to claim 1, wherein Z(i) is represented by the following equation:

$$Z(i) = \{X(i+1) + X(i+2) + \ldots + X(i+m)\} / \tag{1}$$

$$\{X(i-m) + X(i-m+1) + \ldots + X(i-1)\}$$

$$(m = 10 \text{ to } 30).$$

7. The method according to claim 1, wherein the step [3] is performed after i reaches a predetermined calculation start point s.

8. The method according to claim 7, wherein the calculation start point s is a measurement point after a time when a rate of coagulation reaction becomes a maximum.

9. The method according to claim 7, further comprising detecting, as the calculation start point s, a measurement point that is later with V(i)=Vs when a number of measurement points between two points when V(i)=Vs is satisfied exceeds a predetermined value, wherein V(i) is a differential value of the reaction X(i).

10. The method according to claim 7, wherein the calculation start point s is a measurement point after Z(i) acquired in the step [2] has reached a peak of Z(i).

11. The method according to claim 1, wherein the steps [1] and [2] and the steps [3] to [5] are performed in parallel.

* * * * *